United States Patent
Kahn et al.

(10) Patent No.: US 10,945,659 B1
(45) Date of Patent: Mar. 16, 2021

(54) DUAL SLEEP MONITOR

(71) Applicants: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Venkat Easwar, Los Gatos, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 255 days.

(21) Appl. No.: 15/351,386

(22) Filed: Nov. 14, 2016

Related U.S. Application Data

(63) Continuation-in-part of application No. 15/071,189, filed on Mar. 15, 2016.

(60) Provisional application No. 62/133,734, filed on Mar. 16, 2015.

(51) Int. Cl.
*A61B 5/00* (2006.01)
*A61B 5/0205* (2006.01)
*A61M 21/02* (2006.01)
*A61B 5/11* (2006.01)
*A61B 5/024* (2006.01)
*A61B 5/08* (2006.01)

(52) U.S. Cl.
CPC .......... *A61B 5/4815* (2013.01); *A61B 5/0022* (2013.01); *A61B 5/0205* (2013.01); *A61B 5/1102* (2013.01); *A61B 5/4812* (2013.01); *A61B 5/6892* (2013.01); *A61B 5/7275* (2013.01); *A61B 5/7278* (2013.01); *A61M 21/02* (2013.01); *A61B 5/024* (2013.01); *A61B 5/08* (2013.01); *A61B 2560/0223* (2013.01); *A61B 2560/0242* (2013.01); *A61M 2205/3303* (2013.01)

(58) Field of Classification Search
CPC ... A61B 5/4815; A61B 5/4812; A61B 5/4809; A61B 5/4806; A61B 5/6892; A61B 5/0022; A61B 5/0205; A61B 5/1102; A61B 5/7275; A61B 5/7278; A61M 21/02
USPC ................................ 600/587, 595, 300, 301
See application file for complete search history.

(56) References Cited

U.S. PATENT DOCUMENTS

| | | | |
|---|---|---|---|
| 5,168,759 A | 12/1992 | Bowman | |
| 6,231,527 B1 | 5/2001 | Sol | |
| 7,652,581 B2 | 1/2010 | Gentry et al. | |
| 2004/0111039 A1 | 6/2004 | Minamiura et al. | |
| 2005/0076715 A1 | 4/2005 | Kuklis et al. | |
| 2008/0169931 A1* | 7/2008 | Gentry | G08B 21/0461 340/573.1 |

(Continued)

OTHER PUBLICATIONS

"NPL—EasySense LTD", archive.org, accessed: Jan. 7, 2019, published: Nov. 27, 2006.

*Primary Examiner* — Daniel L Cerioni
(74) *Attorney, Agent, or Firm* — NDWE LLP; Judith Szepesi

(57) ABSTRACT

A method and apparatus to receive data from a dual sleep sensor associated with a sleep surface, and analyzing the data to identify sleep phases of one or more users on the sleep surface. In one embodiment, the dual sleep sensor comprises two or more sensors positioned to enable separation of motion data of a first sleeper and a second sleeper.

19 Claims, 19 Drawing Sheets

(56) References Cited

U.S. PATENT DOCUMENTS

| | | |
|---|---|---|
| 2009/0071810 A1 | 3/2009 | Hanson et al. |
| 2010/0036211 A1 | 2/2010 | La et al. |
| 2010/0094139 A1 | 4/2010 | Brauers et al. |
| 2011/0230790 A1* | 9/2011 | Kozlov ............... A61B 5/4812 600/595 |
| 2011/0302720 A1* | 12/2011 | Yakam ............... A61G 7/05776 5/710 |
| 2014/0218187 A1 | 8/2014 | Chun et al. |
| 2015/0015399 A1 | 1/2015 | Gleckler et al. |
| 2015/0101870 A1* | 4/2015 | Gough .................. G01G 3/141 177/211 |
| 2015/0164238 A1* | 6/2015 | Benson ................. G16H 50/30 340/540 |
| 2015/0164438 A1 | 6/2015 | Halperin et al. |
| 2015/0173671 A1* | 6/2015 | Paalasmaa ........... A61B 5/0022 600/301 |
| 2015/0351694 A1 | 12/2015 | Shimizu et al. |
| 2016/0015315 A1* | 1/2016 | Auphan ............... A61B 5/4815 600/301 |
| 2016/0217672 A1* | 7/2016 | Yoon ..................... A61B 5/024 |
| 2017/0020756 A1 | 1/2017 | Hillenbrand et al. |
| 2018/0049701 A1 | 2/2018 | Raisanen |

\* cited by examiner

DUAL SLEEP MONITOR

RELATED APPLICATION

The present application claims priority to U.S. patent application Ser. No. 15/071,189, filed on Mar. 15, 2016, which claims priority to U.S. Provisional Application No. 62/133,734 filed on Mar. 16, 2015. Both applications are incorporated into this application by reference, in their entirety.

FIELD

The present invention relates to sleep, and more particularly to providing sleep analysis.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

BRIEF DESCRIPTION OF THE FIGURES

The present invention is illustrated by way of example, and not by way of limitation, in the figures of the accompanying drawings and in which like reference numerals refer to similar elements and in which:

FIG. 1A is network diagram of one embodiment of the system, including the elements communicated with.

DETAILED DESCRIPTION

An improved sleep analysis system is described. This system can also be referred to as a dual in-bed sensor system. The system includes two or more sensors arranged underneath sleeping surface, such as a mattress, mattress topper, or other portion of the sleeping surface. The sensor portion of the system is designed to be sufficiently flat that the shape of the sensor cannot be felt by a user. In one embodiment, the sensor is sufficiently sensitive to pick up micro-motions when placed underneath or in a mattress, on a box spring, on slats, on or in an adjustable base, on or in a platform or another configuration. In one embodiment, the sensor system can be retrofitted into an existing bed.

In one embodiment, the output of the sensor is coupled to the rest of the sensor system via a cable. In one embodiment, a cable provides power to the sensor, and is used to send data from the sensor to the other parts of the sensor system. In one embodiment, the sensor may be separately powered, and data may be transmitted using a network connection such as Bluetooth or Wi-Fi, or another format. In one embodiment, power and data may both be transmitted wirelessly. In one embodiment, the sensor is coupled to a processor, which is coupled to a mobile device and/or a network. The sensor in one embodiment is designed to have a unit placed under both sides of a mattress designed from two sleepers, such as a queen or king size mattress. The sensors are capable of separating the data from the separate sensors, and identifying the data as belonging to one or the other of the sleepers.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1A:
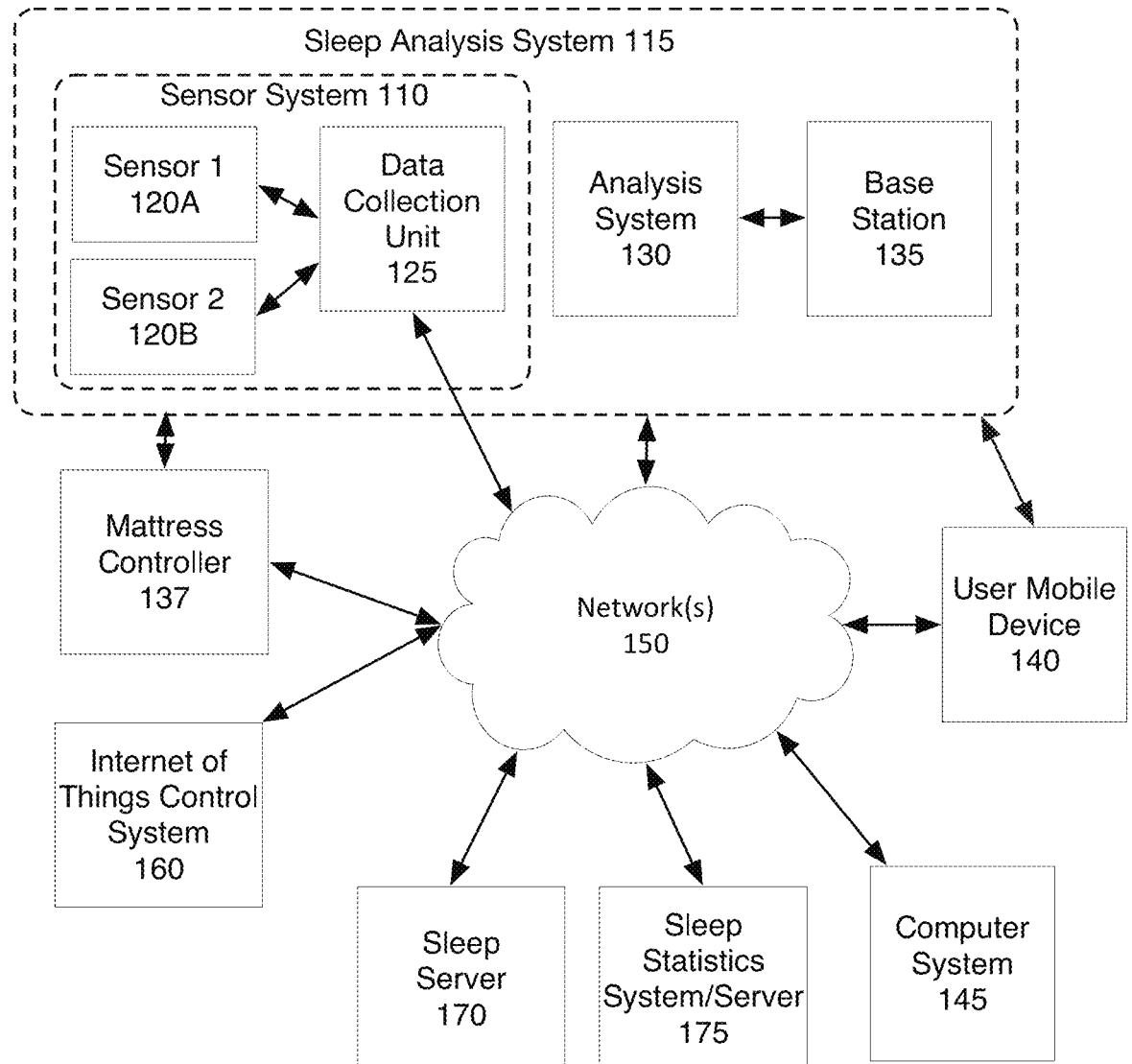

FIG. 1A is network diagram of one embodiment of the system, including the elements, and their communication. The system includes a sensor system 110, which includes sensor 1 120A and sensor 2 120B and data collection unit 125. The sensor system 110 is part of a sleep analysis system 115, which includes sensor system 110, analysis system 130, and base station 135. In one embodiment, the data collection unit 125, analysis system 130, and/or base station 135 may be implemented in the same device. Alternately, the analysis system 130 may be remote and separate from the sensor system 110 and/or the base station 135. In one embodiment, the data collection unit 125 is located within the foundation/mattress/bed, and the analysis system 130 is implemented externally. In one embodiment, the analysis system 130 includes a processor which receives power from a plug-in power supply. In one embodiment, the analysis system 130 has a form factor comparable to a power brick. The base station 135 in one embodiment includes additional sensors. In one embodiment, base station 135 may also include additional user interface features, which may include a microphone, speakers, lights, etc. The base station 135 in one embodiment is located on the bedside table or in a similar location, where it is not blocked by the mattress, as the sensor system 110 is.

In one embodiment, the sleep analysis system 115 communicates with a user mobile device 140. The connection may be made by the analysis system 130 and/or base station 135. The connection between sleep analysis system 115 and user mobile device 140 may be via a network 150, such as via a WiFi connection or cellular network connection. The connection may be via a local area network or personal area network, such as Bluetooth. In one embodiment, the connection may be physical wireline connection. The user mobile device 140 may be a smart phone, a tablet, or another device, which provides additional user interface features and controls. In one embodiment, the connection may be provided through a docking station, or similar connection element, which physically connects to sleep analysis system 115 and the user mobile device 140.

In one embodiment, the sleep analysis system 115 may additionally or alternatively connected to a computer system 145 or a server 170, via network 150, such as Bluetooth, WiFi, or another type of connection. In one embodiment, the user mobile device 140 and/or the sleep analysis system 115 may provide controls to devices which are part of the Internet of Things 160. The Internet of Things 160 may include elements of a smart home, or environment, and provide controllers for a smart bed, lights, thermostats, coffee makers, window treatments, speakers, alarm clocks, and other aspects of the user's environment that may be controlled via commands through a network. The IoT system 160 may control IoT enabled elements to assist in optimizing the user's sleep and health.

In one embodiment, some or all of the user data may further be transmitted to a sleep server 170, which can provide additional analysis, in one embodiment. In one embodiment, user data is stored on the mobile device. In one embodiment, collective anonymized user data is stored by sleep statistics system/server 175. The sleep statistics system/server 175 utilizes the abstracted data to analyze sleep patterns across large populations, in embodiments correlated by user characteristics, environmental characteristics, and/or other data. The sleep statistics system/server 175 in one embodiment, includes data from millions of nights of sleep, and uses that data to provide recommendations to users and adjustments to the system.

Figure 1B:
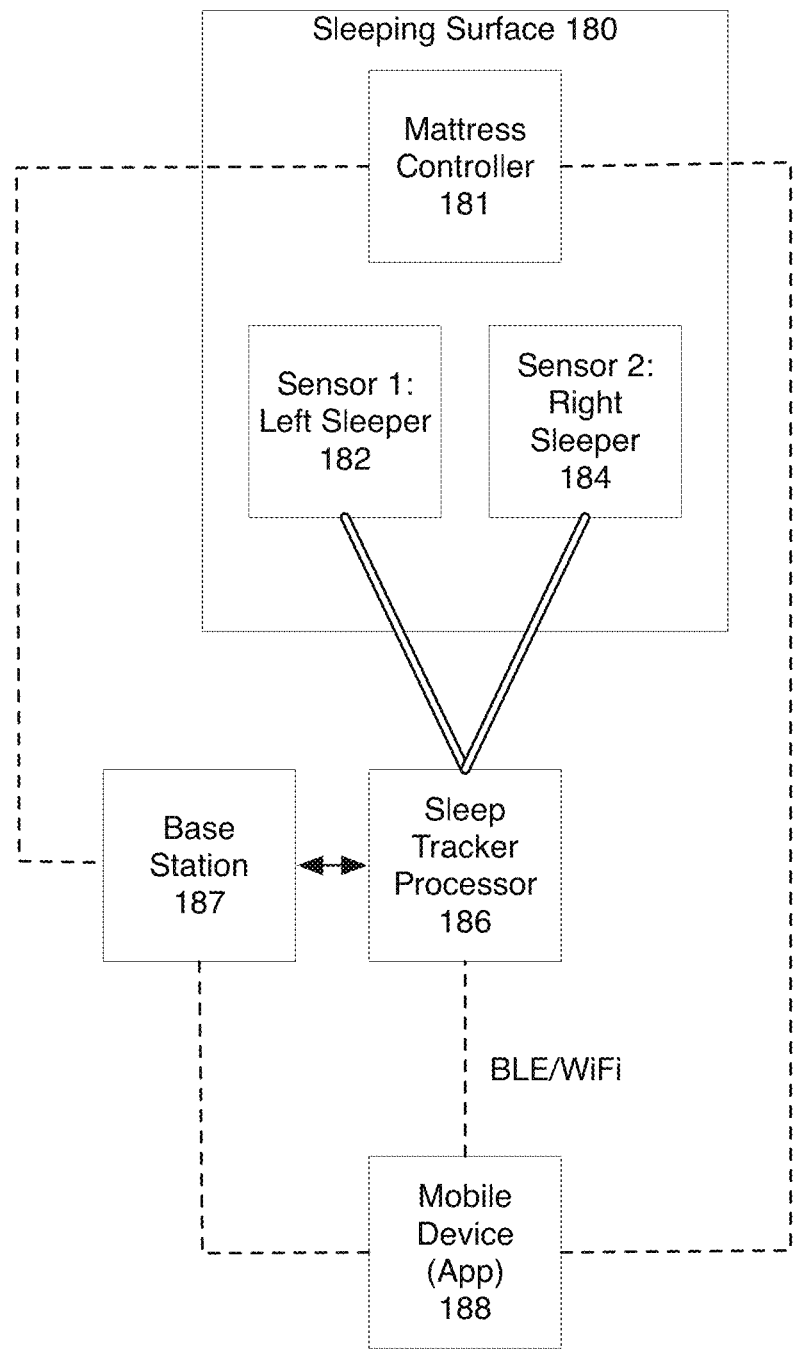
FIG. 1B is a diagram showing the configuration of the system, according to one embodiment

FIG. 1B is a diagram showing the configuration of the system, according to one embodiment The sleep surface 180 includes two sensors, in one embodiment, sensor 1 for the left sleeper 182, and sensor 2 for the right sleeper 184. The sensors 182, 184 are coupled to a sleep tracker processor 186. The sleep tracker processor 186, in one embodiment, corresponds to data collection unit 125 and analysis system 130. In one embodiment, each sensor 182, 184 has a cable coupling it to the sleep tracker processor 186. In another embodiment, one sensor 184 is coupled to the other sensor 182, which in turn is coupled to the sleep tracker processor 186, meaning that only one cable extends from the bed. In one embodiment, the connection between the sensor(s) 182/184 and the sleep tracker processor 186 is a CAT5 cable, using an RJ45 plug in the sleep tracker processor 186 and sensor(s) 182, 184. The connection, in one embodiment, provides power to the sensors 182, 184, and sends data from the sensors 182, 184 to the sleep tracker processor 186. In one embodiment, base station 187 may also send data to sleep tracker processor 186. Base station 187 may include additional sensors, as noted above.

The sleep tracker processor 186 in one embodiment connects to an application on a mobile device 188 via a wireless connection. In one embodiment, the wireless connection is a low-power Bluetooth (BLE) connection. The connection may be continuous, periodic, or intermittent. In another embodiment, the connection is a Wi-Fi connection, or another type of wireless connection. In one embodiment, the mobile device 188 may be connected to the sleep tracker processor 186 via a wired connection. Base station 187 may connect to mobile device 188 in addition to, or instead of, sleep tracker processor 186.

In one embodiment, the mobile device 188 or the base station 187 may communicate with a mattress controller 181. The mattress controller 181 may adjust the mattress configuration which may include one or more of angle, temperature, and firmness. Each of these may be adjusted on a per segment basis (e.g. angle, temperature, and firmness may vary across the mattress, between sleepers and within the sleep surface in contact with the different body parts of a single sleeper.)

Figure 1C:
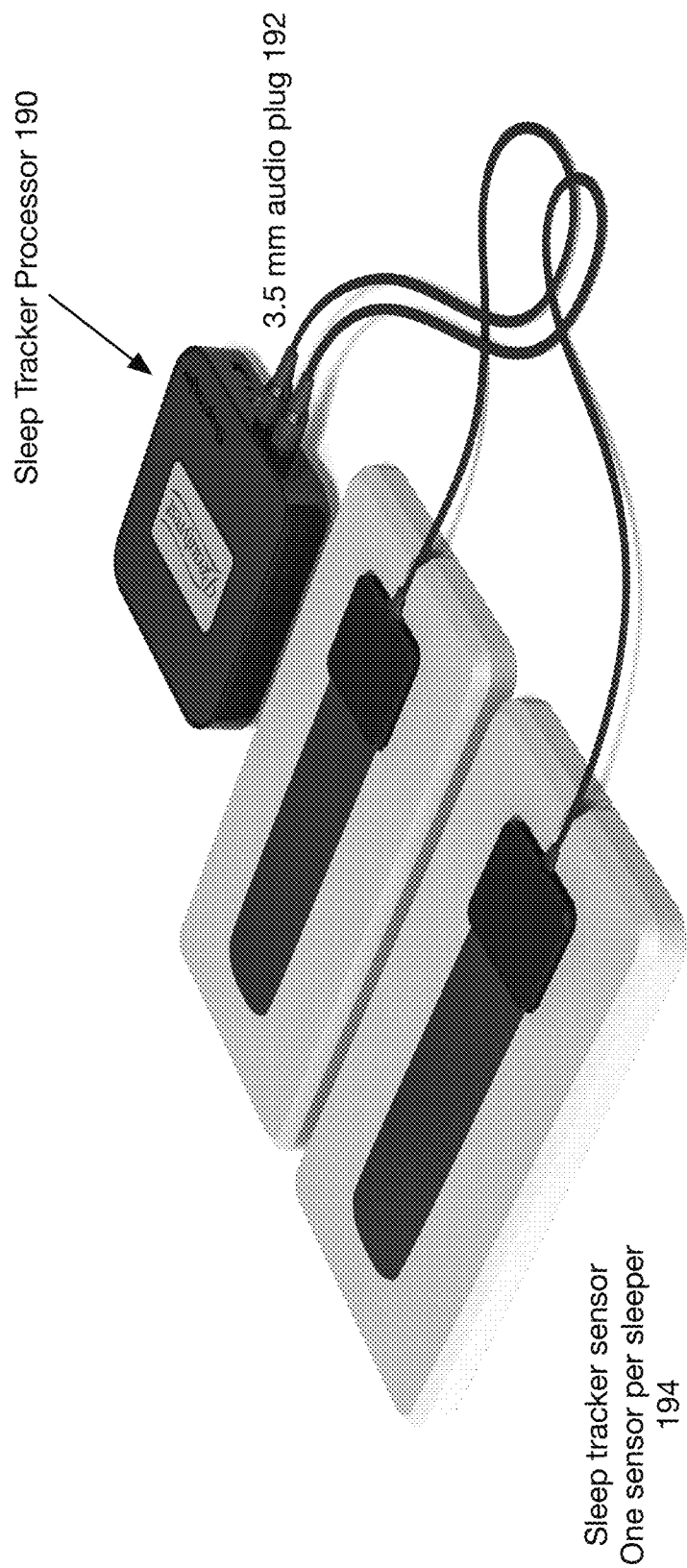
FIG. 1C is an illustration of one embodiment of the sensor and processor of the system.

FIG. 1C illustrates one embodiment of a sleep analysis system. The system includes two sleep tracker sensors 194, and a sleep tracker processor 190, into which the sensors are plugged. In one embodiment 3.5 mm audio plugs are used for this connection. This provides power to the sensors, and receives data from the sensors to the sleep tracker processor 190. In one embodiment, the sensors are piezoelectric sensors. In one embodiment, the sensors are designed to be placed near the head of the user, and are capable of picking up micro-movements not only representing the user's movements in bed, but also the users' heart rate and breathing. In one embodiment, each sensor consists of a flat portion which includes the piezoelectric sensor, and is made of semi-rigid plastic, and a case which includes the processing and connection elements. In one embodiment, the length of the plastic and sensor is less than 16". In one embodiment, the sensor is attached to a hard foam base, which provides a deformable solid base, enabling the sensors to be placed on any surface, including slats, foundations, adjustable bed frames, etc. The foam, in one embodiment is closed cell foam.

Figure 1E:
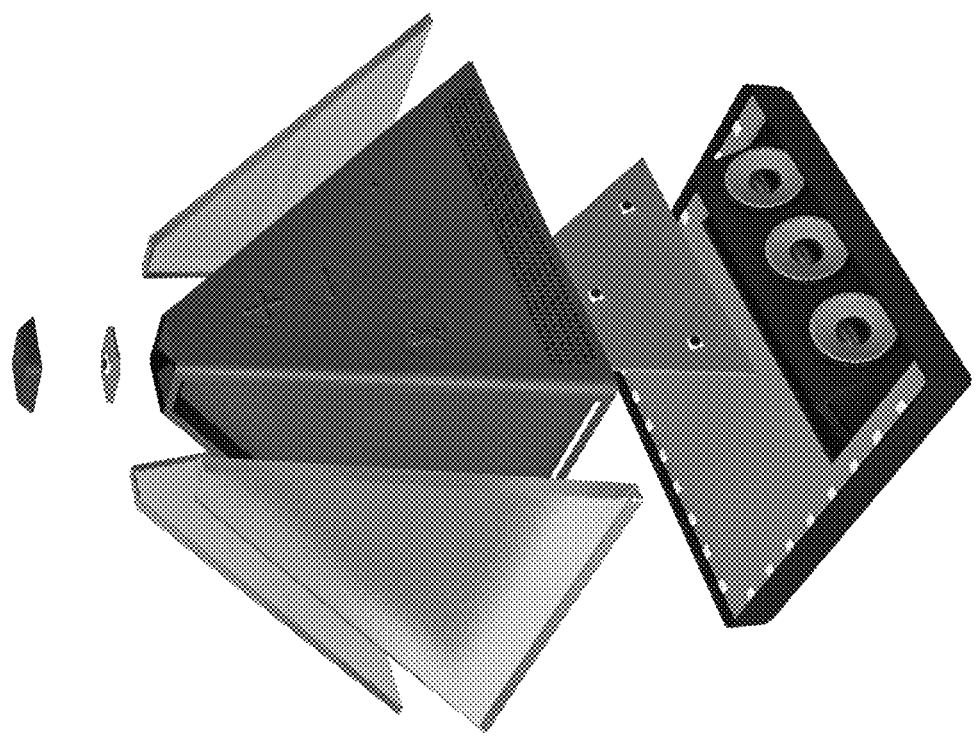
FIGS. 1D and 1E are illustrations of one embodiment of a base station.
Figure 1D:
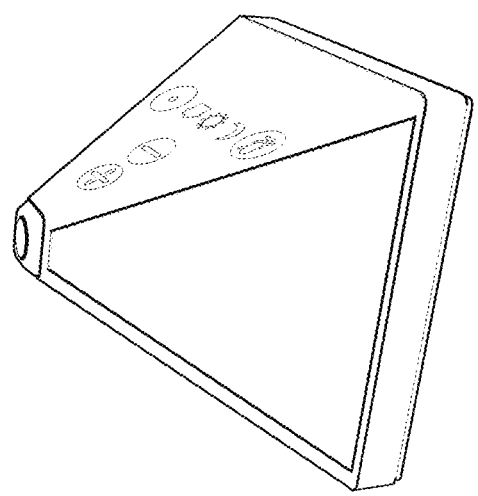

FIGS. 1D and 1E illustrate one embodiment of a base station. The base station may be a pyramid designed to provide an interactive element without the use of the mobile device. In one embodiment, the base station is an add-on element, that is not necessary for the functioning of the system, but provides additional functionality. In one embodiment, the base station provides sensors to measure and evaluate air quality, light, sound, and temperature in the room. In one embodiment, it may also provide output user interface of light (in one embodiment adjustable light temperature and brightness) and sound (white noise and/or music and/or alarms).

In one embodiment, it also includes a microphone to provide a voice controlled interface. In one embodiment, the base station implements a voice and IoT control system such as AMAZON ALEXA™ or GOOGLE HOME™ or APPLE SIRI™ natively to enable control of IoT elements. In one embodiment, the base station provides complete control of the sleep system and paired IoT systems without requiring a mobile phone to be available. Additionally, light, air quality, temperature, and sounds have correlations to sleep. The base station's additional sensors are able to collect this data. In one embodiment, the base station provides an extended night stand functionality with additional sensors, and optionally additional processing power. In one embodiment, the base station connects to the sleep tracker processor.

Figure 2A:
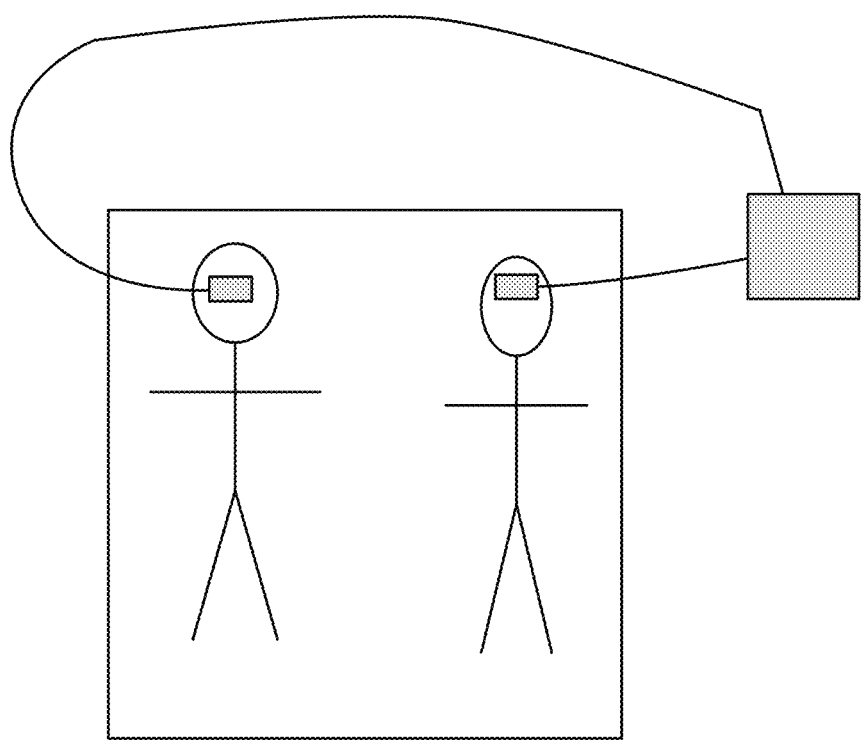
FIG. 2A is an illustration of one embodiment of the positioning of the sensors for the sleeping surface, to monitor two sleepers.

FIG. 2A illustrates the positioning of the two sensor modules in a typical configuration. The sensor modules are designed to be positioned at the head of the bed, under the user's pillow, and in one embodiment are designed to be smaller than the user's head. This reduces the noise of breathing, which otherwise can overwhelm the data collected, and make it difficult to recognize micro-movements and/or heart data. It also makes it easier to perform data separation to identify data for each of the users. Additionally, this position makes it possible to perform data correlation, for a single sleeper, regardless of where on the bed the sleeper lies.

Figure 2B:
FIG. 2B is a diagram of one embodiment of various sleep configurations, which may be recognized by the system.

FIG. 2B is a diagram of one embodiment of various sleep configurations, which may be recognized by the system. The system in one embodiment is designed to identify the user sleep configuration of two users sharing a bed. Sleep configurations, in one embodiment include sleeping on the right side, left side, stomach, and back. In one embodiment, the system can differentiate the sleep configurations of both users, identifying the sixteen possible configurations illustrated in FIG. 2B. In one embodiment, additional configuration information may also be identified, for example the system may identify more details about the user's sleep configuration, such as how tightly the user is curled, the relative locations of the user's legs etc. The more data is available about the user's sleep, the more data can be used in correlating sleep state data and sleep quality.

Figure 3:
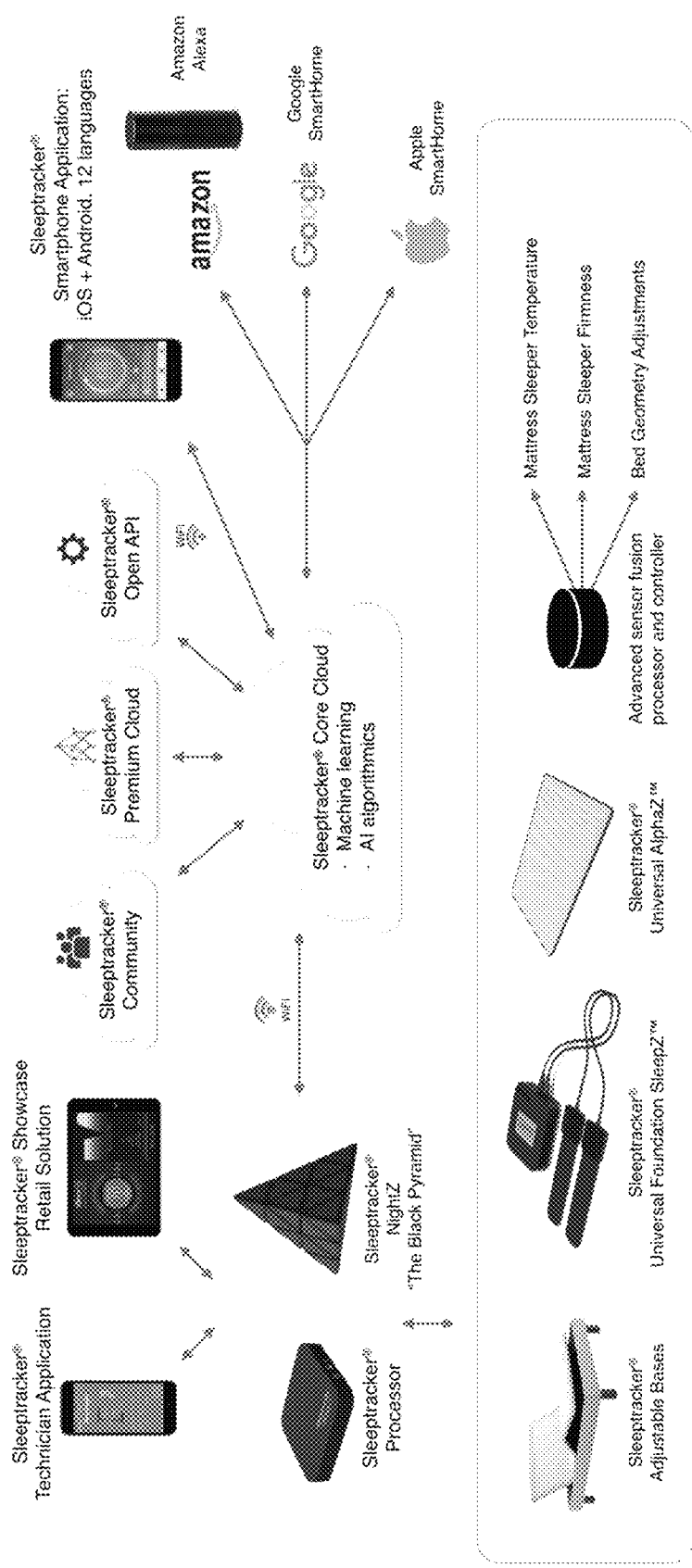
FIG. 3 is a system diagram showing one embodiment of the various elements which may interact with the system.

FIG. 3 is an exemplary system which may be used with the sleep monitoring system. The sleep tracker may be built into the base of a bed, slipped under a mattress or mattress topper, built into a fixed bed base. As noted above, the base station may provide additional sensor data. This data is sent to the sleep tracker processor. The sleep tracker processor sends the data to the cloud, in one embodiment. The "cloud" may perform some of the analytics to provide useful data to the user. The "cloud" in this context may be a server computer, a set of distributed servers, or any other configuration of processing power which is remote from the sleep tracker and available via a network.

In one embodiment, the cloud also utilizes machine learning and artificial intelligence (AI) algorithmics to enable extraction of relevant data from the information collected by a multitude of users. In one embodiment, there may also be a community aspect, through the core cloud. Users may log into the community, share information, get recommendations, download configurations for the IoT/home systems/mattresses/beds/sleep patterns, etc. In one embodiment, there is an open API (application programming interface) which enables interaction with Smart Home systems—show as from AMAZON, GOOGLE, and APPLE, but of course may be from any vendor. In one embodiment, there may also be a smart phone application, available to the user.

In one embodiment, the sleep tracker processor may interact directly with a smart phone application, or may interact with the smart phone via the cloud. The smart phone, the sleep tracker processor, and/or the base station may be used to control a smart home. In one embodiment the system may interact with IoT (Internet of Things) systems, which provide control over various aspects of the home. These controls may include altering lighting, temperature, air filtration, humidifiers, etc. In one embodiment, controls may also include things such as switching on a coffee pot, or setting smart alarms, locking doors, turning off stoves, etc.

Figure 4:
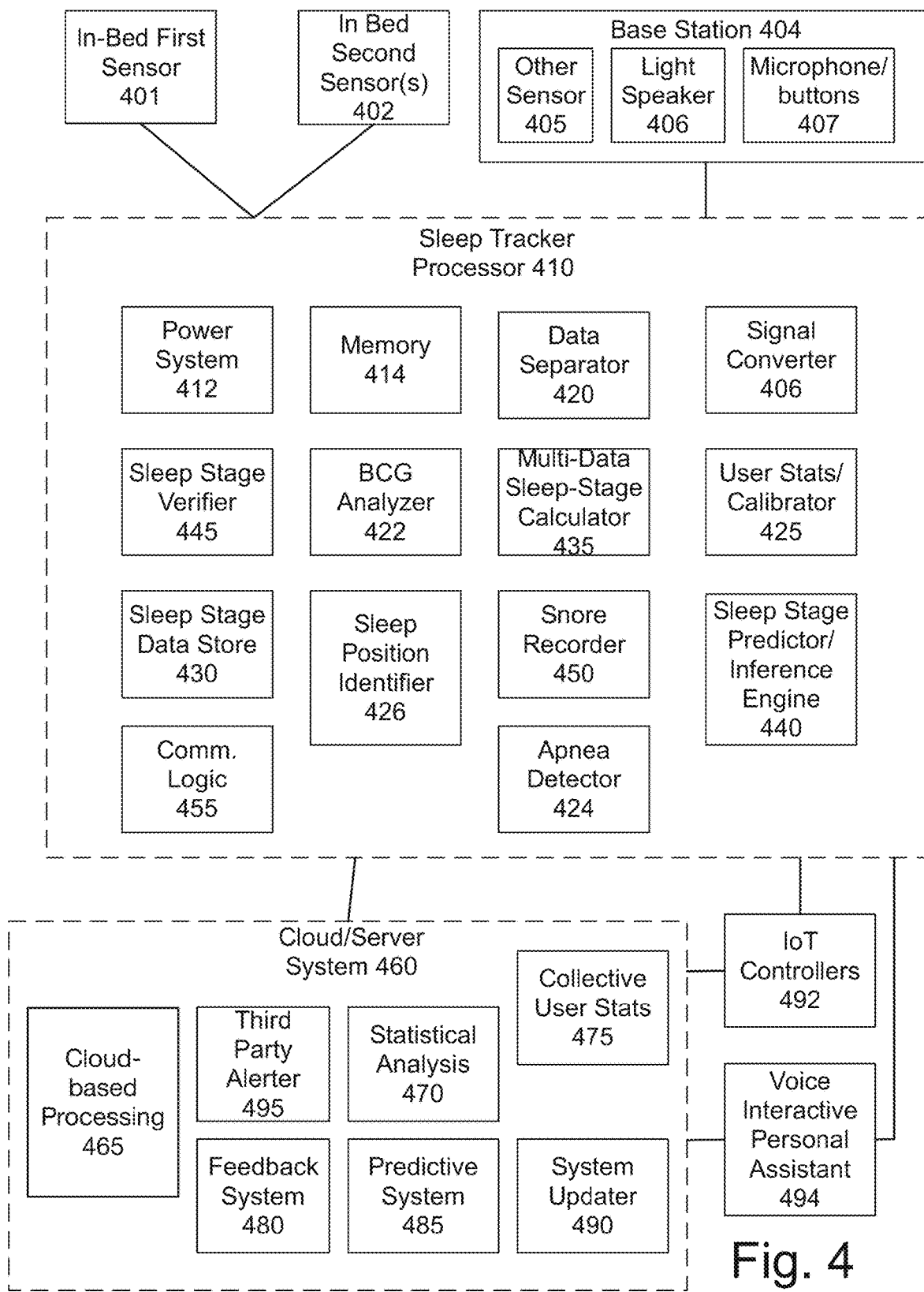
FIG. 4 is a block diagram of one embodiment of the sensor system and computer system.

FIG. 4 is a block diagram of one embodiment of the sleep detection system sensor system and cloud/server system. The system includes in one embodiment two in-bed sensors 401, 402. In one embodiment, the sensors are piezoelectric sensors. In one embodiment, each sensor is designed to be under one portion of a bed, when there are two sleepers. In one embodiment, a single sensor system may be used for a single sleeper. In one embodiment, there may be additional sensors as well. The sensors 401, 402 are coupled to a sleep tracker processor 410.

A base station 404 is also coupled to the sleep tracker processor 410. The base station 404 provides additional sensors 405. The additional sensors may include, in one embodiment, one or more of: temperature sensor, light sensor, air quality sensor, sound sensor, humidity sensor. Additional sensors to evaluate the user's environment may also be included.

In one embodiment, base station 404 also includes input/output features. Input features may include a microphone for voice control as well as a variety of buttons and/or knobs. Output features may include lights and speakers.

Sleep tracker processor 410 includes a power system 412 in one embodiment, to step down the AC voltage from the plug to a level that the sensors 401, 402 need. In one embodiment, an power system 412 provides power for the elements of the sleep tracker processor 410, including the processor. In one embodiment, base station 404 receive power from sleep tracker processor. Alternatively, base station 404 may be separately powered.

The output of the sensors 401, 402, may be converted by a signal converter to a digital signal, prior to being sent to the sleep tracker processor 410 via a wired connection. In one embodiment, sensors 401, 402 include a local data store to buffer sensor data. In another embodiment, the raw sensor data is continuously transmitted to sleep tracker sensor 410, and processed in the sleep tracker sensor 410. Base station 404 may have some internal processing of the signals, or may also transmit the signals directly to the sleep tracker processor 410 for processing.

In one embodiment, the sensors 401, 402 include a piezoelectric sensor and signal converter 406, and are powered through a cable from the sleep tracker processor 410. The converted signal is sent to the sleep tracker processor 410, which in one embodiment is plugged into the wall. In another embodiment, the raw sensor data may be sent to sleep tracker processor 410.

Sensors data is, in one embodiment, stored in memory 414. In one embodiment, signal converter 406 converts the raw data from sensors 401, 402, 405, prior to storing it in memory 414.

The data separator 420 separates the data from a plurality of sensors, if there are multiple sleepers. The data separator 420 in one embodiment further separates the breathing, micro-motion, and heart rate data. The data is then used by sleep position identifier 426 to identify the sleep position of each of the users in the bed.

BCG analyzer 422 analyzes the separated heart data. BCG is ballistocardiograph which measures the movements of the body caused by the shifts in the center of mass of the blood and to a lesser extent of the heart. This data may be generally used to help identify sleep state. However, it can also be used to detect potential problems, such as arrhythmia.

Apnea detector 424 utilizes the breathing data to ensure that the user is breathing smoothly. Snore recorder 450 in one embodiment utilizes a microphone to record snoring. In one embodiment, snore recorder 450 receives data from base station 404, which includes a microphone. In one embodiment, the snore recorder 450 may include a detection mechanism and a trigger to turn on the microphone and recording when appropriate based on breathing data.

Multi-data sleep-state calculator 435 utilizes the heart rate, breathing, and micro-motion data, as well as any other data available, to identify the users' sleep states. In one embodiment, sleep-stage calculator 430 data is compared to the output of sleep stage predictor/inference engine 440 by sleep stage verifier 445. The real data is used to validate the prediction, rather than generate the sleep state directly from the data. In one embodiment, the inference engine 434 may utilize primarily the user's own data, from data store 430. However, in one embodiment, data collected over many users may be used to initially populate inference engine's 440 data set. Sleep stage data store 430 stores the current & past sleep state data. This may be used by the inference engine 440, as well as communicated to computer system 460, which may be the user's mobile device or the server system. In one embodiment, mismatch between real data and predicted data may be used by user stats/calibrator 425 to adjust the inference engine 440. In one embodiment, user stats/calibrator 425 may also include relevant user data such as age, sex, health status, activity level, etc. In one embodiment, this data may be entered by the user, or collected by other systems. For example, in one embodiment, user activity data may be collected from an activity monitor, such as the one described in U.S. Patent No. XYZ, which is incorporated herein by reference. In addition to user data, the user stats 425 may also include environmental data, which includes information such as time of sunrise and sunset, temperatures, etc. In one embodiment, this data is sent to computer system 460.

In one embodiment, connection between sleep tracker processor 410 and cloud/server system 460 through communication logic 455 is intermittent, and the sleep tracker processor 410 does not rely on the computer system 460 for calculations or processing. In another embodiment, one or more of the logics described may either be on the computer system 460, either on a mobile device, shared with the mobile device such that the combination of the sleep tracker processor 410 and the mobile device 450 make the described calculations, or on a remote server system. Cloud-based processing 465 may provide some or all of the functionality described above with respect to the sleep tracker processor 410. In one embodiment, the sleep tracker processor 410 performs preliminary data analytics and cleanup, and the detailed processing is done via cloud-based processing 465.

In one embodiment sleep tracker processor 410 further includes mattress controls 442 to control the mattress based on sleep stage and any other detected issues. Additionally, sleep tracker processor 410 may in one embodiment include alert system 444. In another embodiment, these logics may be part of mobile device 450.

Cloud/Server system 460 receives data from sleep tracker processor 410, via its own communication logic. In one embodiment, the data is used by the Cloud/Server system 460 to perform statistical analysis 470 on the data. Predictive system 485, in one embodiment, predicts future health issues. In one embodiment, the predictive system utilizes historical data and data from collective user statistics 475 from multiple users to make smart predictions.

Feedback system 480 utilizes the graphic display capabilities of the computer device 460 (either mobile device or web page made available via server) to provide detailed feedback to the user about their sleep, and other data, in one embodiment.

In one embodiment, sleep tracker processor 410 connects to Cloud/Server system 460 either directly or through mobile device. Server system collects anonymized user statistics and provides a machine learning based, high power big data analytics system, to make predictions, which may be provided to the user's system, and shown to the user. The predictions may be provided to the user as recommendations. For example, if the system determines that when users sleep less than 6 hours a day for more than 3 days in a row, they are much more likely to get ill, it may warn the user prior to that threshold being met that he or she needs to sleep more.

In one embodiment, Cloud/Server system 460 also includes system updater 490 which may push updates to sensors, base station, and/or sleep tracker processor 410. This remote update capability means not only that the calibration and prediction is accurate, but also that if a problem is discovered it can be remedied without requiring access to the system by IT personnel.

In one embodiment, sleep tracker processor 410 and/or computer system 460 communicates with Internet of Things (IoT) controllers 492. Alternately or additionally such controls may be within base station 404. This enables adjustment of the user's environment to optimize sleep and minimize health risks.

In one embodiment, sleep tracker processor 410 and/or computer system 460 communicates with a voice interactive personal assistant such as AMAZON ALEXA™. In one embodiment, the base station 404 may be used to communicate with such an assistant. In one embodiment, the base station 404 includes a native implementation of the assistant.

Figure 5:
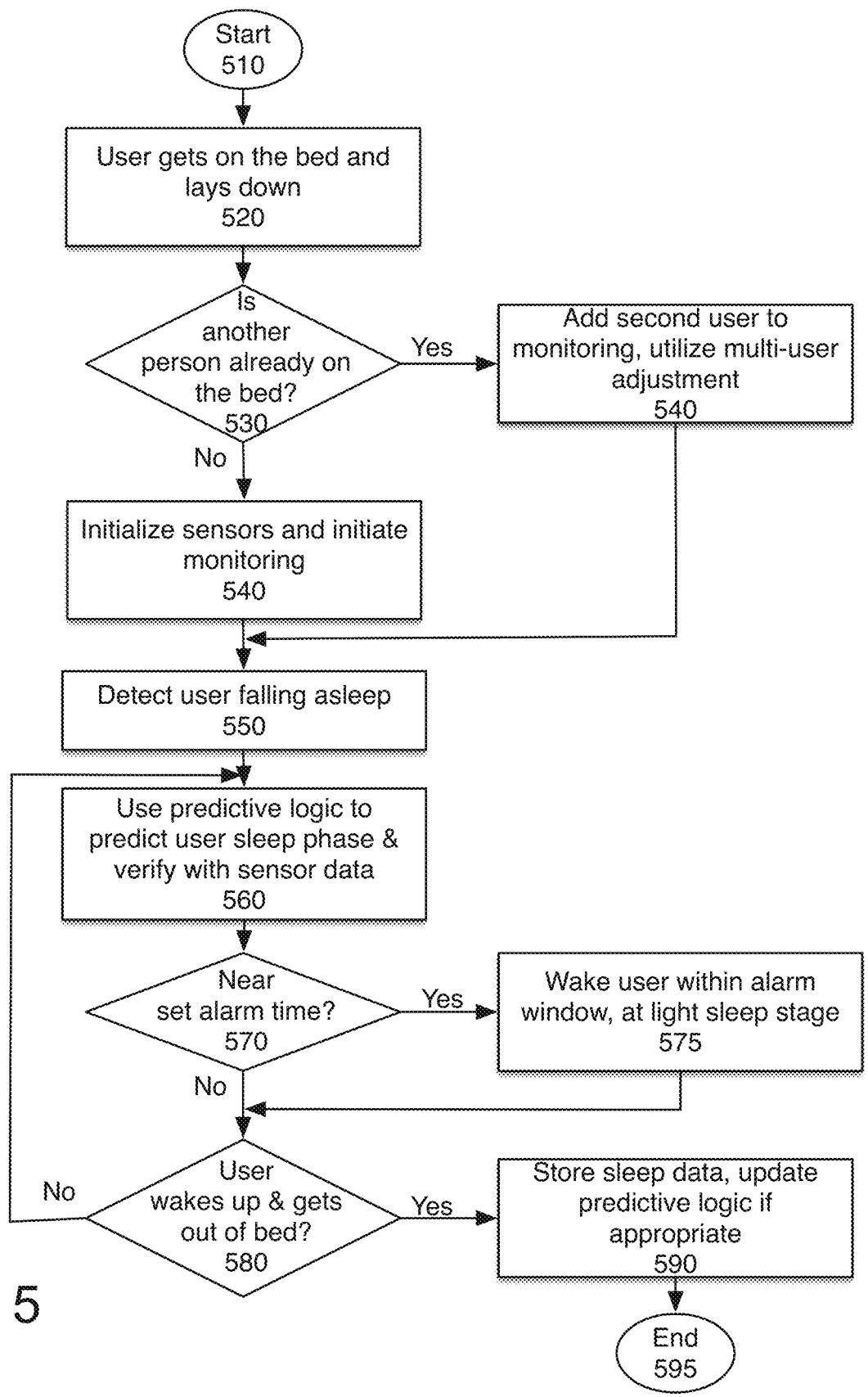
FIG. 5 is a flowchart of one embodiment of using the system.

FIG. 5 is a flowchart of one embodiment of using the system. The process starts at block 510. In one embodiment, this process is initiated when the system is turned on.

At block 520, the user gets on the bed, and lays down. In one embodiment, the system detects the user getting on the bed, as well as identifying when the user lays down.

At block 530, the process determines whether there is another person on the bed already. If so, the second user is added to the monitoring, and multi-user adjustment is utilized, at block 540. Multi-user adjustment monitors the relative data between the users to accurately attribute data to the correct user. Because the sensor is very sensitive, a sensor on the right side of the bed is capable of picking up movement from the user laying on the left side of the bed. In one embodiment, the system takes data from both sensors, subtracts the "non-local" data from its sensor (e.g. the contribution that reflects the other sensor's data), and then utilizes that differential data set to evaluate the user's status.

If there was no other user on the bed, at block 540 the sensors are initialized and monitoring is initiated in one embodiment. In one embodiment, initializing the sensor includes calibration. In one embodiment, the sensor is calibrated each time a person gets onto the bed. In one embodiment, if the bedframe is adjustable, when the bedframe is adjusted the sensor is recalibrated. In one embodiment, the system can be utilized for a fully adjustable bed, such as the Simmons NuFlex Adjustable Bed Base™, which can be positioned at many angles with a moveable head and foot portion. Because the sensor system is built into the base, in one embodiment, and calibrates when the bed is reconfigured, it can be used regardless of the positioning of an adjustable bed. In another embodiment, the system may continuously monitor and calibrate sensors, and this step may be skipped.

At block 550, the process detects the user falling asleep. When the user falls asleep the movements, and heart rate change, and this is used to detect the user falling asleep. In one embodiment, the user may indicate on the mobile device or base station that he or she is falling asleep, and this indication may be detected.

At block 560, the system uses predictive logic to predict the user's sleep phase, and verifying the predicted state using sensor data. The use of the predictive logic reduces the processing time and complexity for correctly identifying the user's sleep state and status.

At block 570, the process determines whether it's near the alarm time. If it is near the alarm time, at block 575, the user is woken within the alarm window, at a light sleep stage, as detected by the system. The process continues to block 580. If it's not near the alarm time, the process continues directly to block 580.

At block 580, the process determines whether the user woke up and got out of bed. If so, at block 590, the sleep data is stored. In one embodiment, the predictive logic is updated, if needed. In one embodiment, the predictive logic is customized based on data about the user. Therefore, as additional data is acquired, the predictive logic is continuously updated to ensure that the system correctly predicts and responds to the user's sleep states. In one embodiment, the system can also monitor the user's health, and can respond to that data appropriately as well. The process then ends at block 595.

If the user has not woken up and gotten out of bed, at block 580, the process continues to use predictive logic and monitor the user's state. In one embodiment, this may continue even after an alarm. In one embodiment, if the user does not get out of bed with an alarm, the system may adjust the alarm settings to increase the likelihood that the user will wake up and get out of bed.

Figure 6:
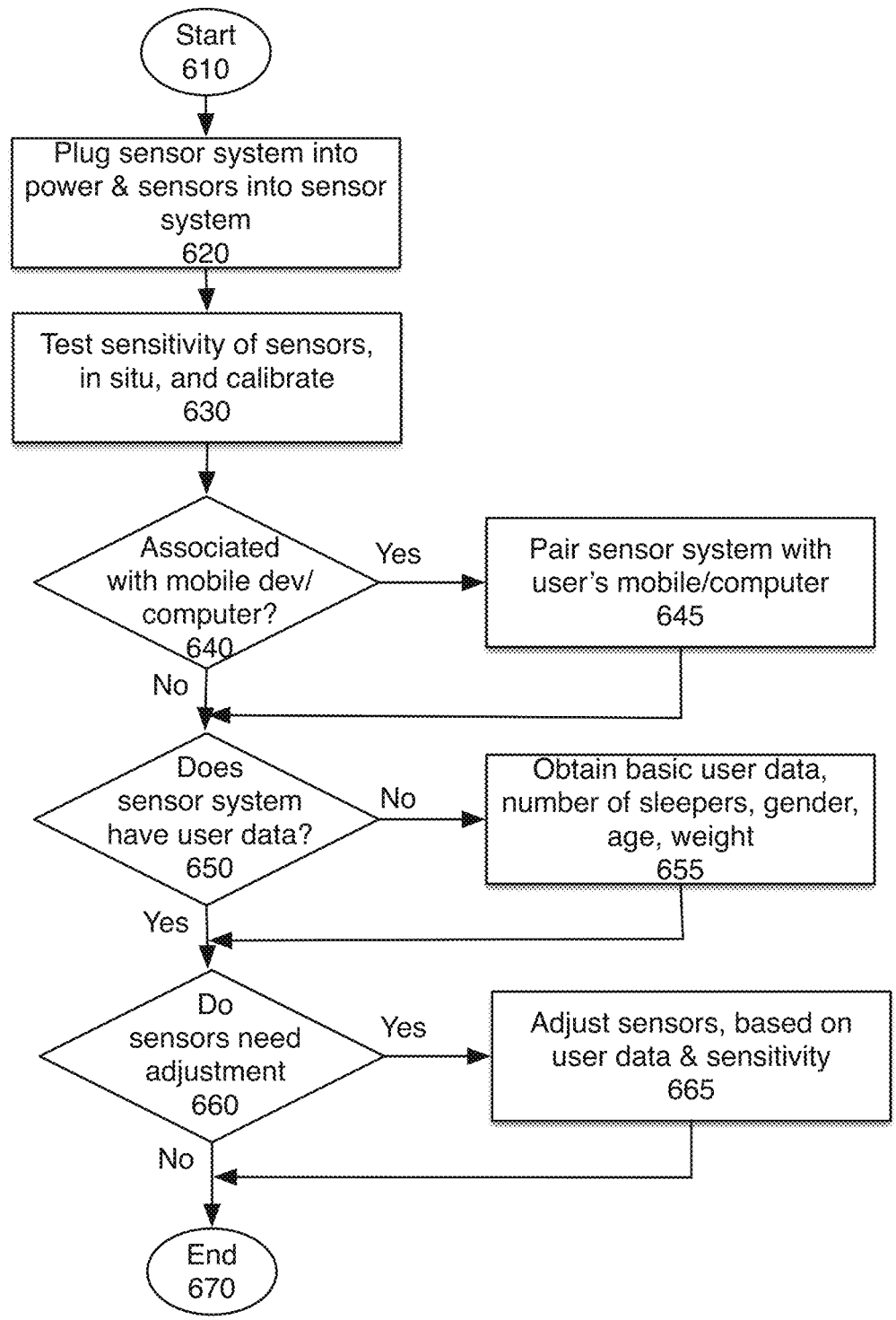
FIG. 6 is a flowchart of one embodiment of configuring the system.

FIG. 6 is a flowchart of one embodiment of configuring the system. The process starts at block 610. In one embodiment, this process takes place when the system initially is set up.

At block 620, the data collection unit is plugged into power, and the sensors are plugged into the data collection unit. In one embodiment, the sensors are connected to the data collection unit via a CAT5 cable. In another embodiment, a separate power cable and data cable is used. In one embodiment, a 3 mm audio cable is used.

At block 630, the sensitivity of the sensors is tested in situ. In one embodiment, once the sensor is in place (e.g. in its final location) its sensitivity is tested, and it is calibrated. Calibration ensures that the sensor is functional. In one embodiment, if there is a problem, the system a message may be sent to get any issues corrected. In one embodiment, calibration is a self-calibration.

At block 640, the process determines whether the system has been associated with a mobile device, application, or computer. In one embodiment, the system is designed to be paired with a device that provides additional user interface features. If the system has not yet associated, the process at block 645 pairs the sensor system with the user's mobile device, computer, or application. The process then continues to block 650. In one embodiment, the system uses a Bluetooth local area network, and utilizes standard Bluetooth discover methods.

At block 650, the process determines whether the sensor system has user data. User data, in one embodiment, includes user characteristic data. In one embodiment, characteristic data may include one or more of the user's gender, age, height, health, and athletic ability. In one embodiment, this data may be available from the paired device. For example, if the user has an existing health application on the user's mobile device, this data may be available. The user may also have added this data to the application already, or this data may be collected when the user logs into the system for configuration.

At block 655, the basic user data is obtained. In one embodiment, basic user data may include user characteristics as well as usage characteristics. Usage characteristics indicate the number of sleepers on the bed, and in one embodiment the sleep configuration. Sleep configuration indicates where each user sleeps, and which position they sleep in. In one embodiment, the system requests this data from the user. The process then continues to block 660.

At block 660, the process determines whether the sensors need adjustment. In one embodiment, this determination is made based on the user data and sensor calibration and sensitivity data. If the sensors do not need adjustment, the process ends at block 670. If the sensor needs adjustment at block 665, the sensor is adjusted. In one embodiment, the sensor adjustment may be based on user weight and sleep position, as well as sleep configuration data. In one embodiment, the adjustment reduces sensitivity for a larger user, and increases sensitivity for a smaller user. Other types of adjustments available in the sensor system may be used. After a sensor adjustment, the sensor recalibrates itself. The process then ends at block 670.

Figure 7A:
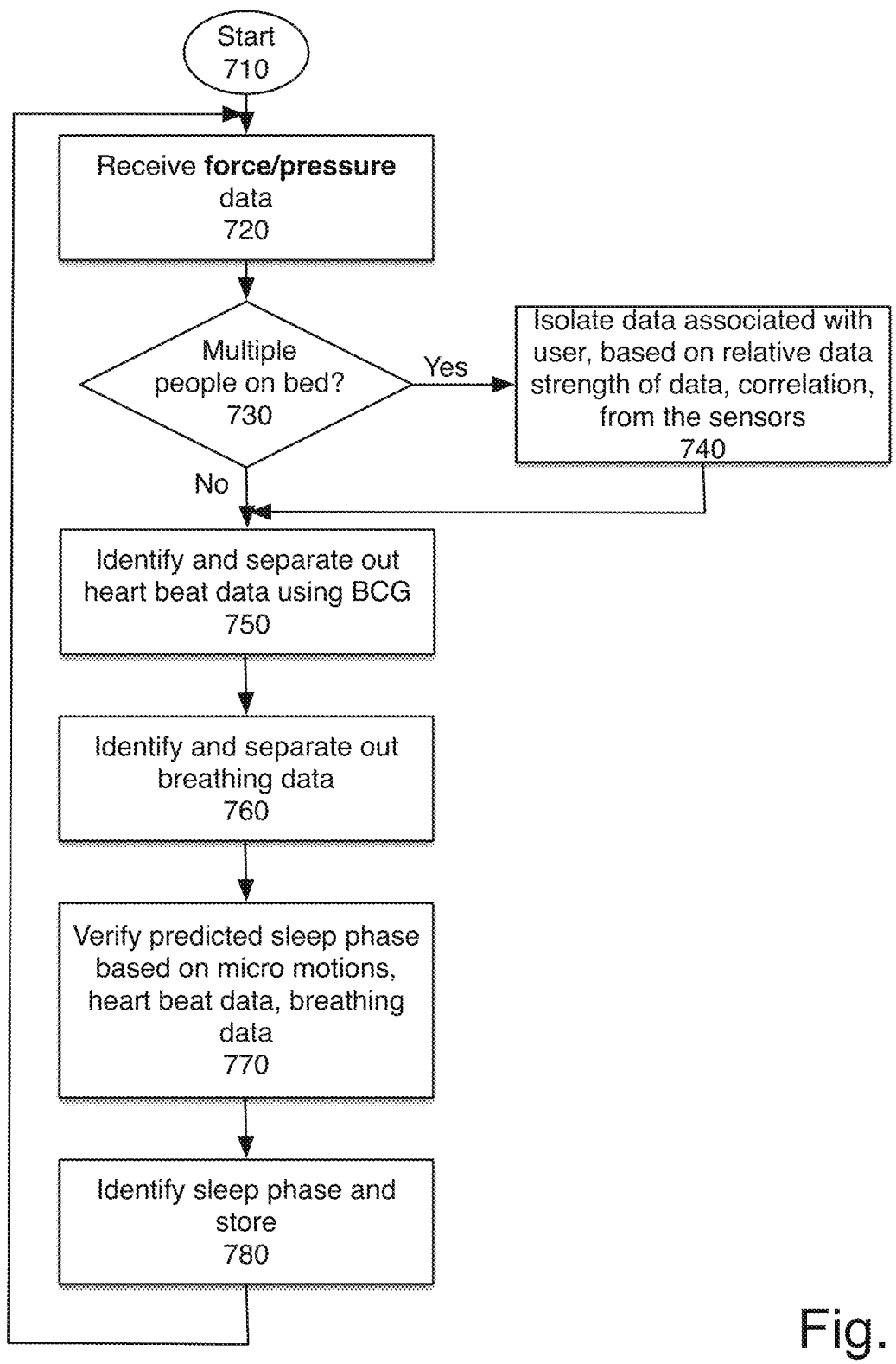
FIG. 7A is a flowchart of one embodiment of generating data from the sensor system.

FIG. 7A is a flowchart of one embodiment of generating data from the sensor system. The process starts at block 710. In one embodiment, this process runs continuously when the user is sleeping.

At block 720, the system receives force/pressure data from the piezoelectric sensors. In one embodiment, data is received from both sensors. In one embodiment, additional data may also be received from other sensors, such as a wristband, or mobile device. In one embodiment, data from multiple devices may be combined to generate the complete data.

At block 730, the process determines whether there are multiple people on the bed. When there are multiple people on the bed, the system must isolate data for each user, to be able to evaluate the user's sleep.

If there are multiple people on the bed, at block 740, the data is isolated, based on the relative data strength received from the sensors. As a general rule, both sensors will detect movement by anyone on the bed. However, the sensor in closer proximity to the user will sense a stronger movement from the same heart beat, breath, or micro-motion. Therefore, the relative signal strength, and correlation and difference between the sensor data s detected by multiple sensors is used to isolate the data associated with each user. The process then continues to block 750. If there are not multiple people on the bed, then process continues directly to block 750.

At block 750, the heart beat data is isolated. Each heart beat moves the user's body slightly. The heart beat is the cardiac cycle, including diastole, systole, and intervening pause. Heart beats are generally at a particular frequency, called the heart rate. The heart rate slows during sleep but does not generally change quickly. Therefore, the heart beat data can be isolated based on the known heart rate, and the cardiac cycle information, using BCG.

At block 760, the breathing data is separated out. Each breath inflates the user's lungs and thus causes motion in the mattress. Breathing is also rhythmic, and includes the contraction and flattening of the diaphragm, and the relaxation of the diaphragm. Breathing is generally slowed in deeper sleep, however the rhythmic pattern of breathing continues. This data is used to separate out breathing data.

Once breathing data and heart beat data are identified in the motion data, and filtered from the data set, the remaining information is the micro-motions made by the user in sleep and any medical indications.

At block 770, the combination of micro-motion data, heart beat data, and breathing data is used to determine the user's sleep phase, or verify the predicted sleep phase. At block 780, the appropriate sleep phase is identified. The process then stores this data, and returns to block 720 to continue monitoring.

Figure 7B:
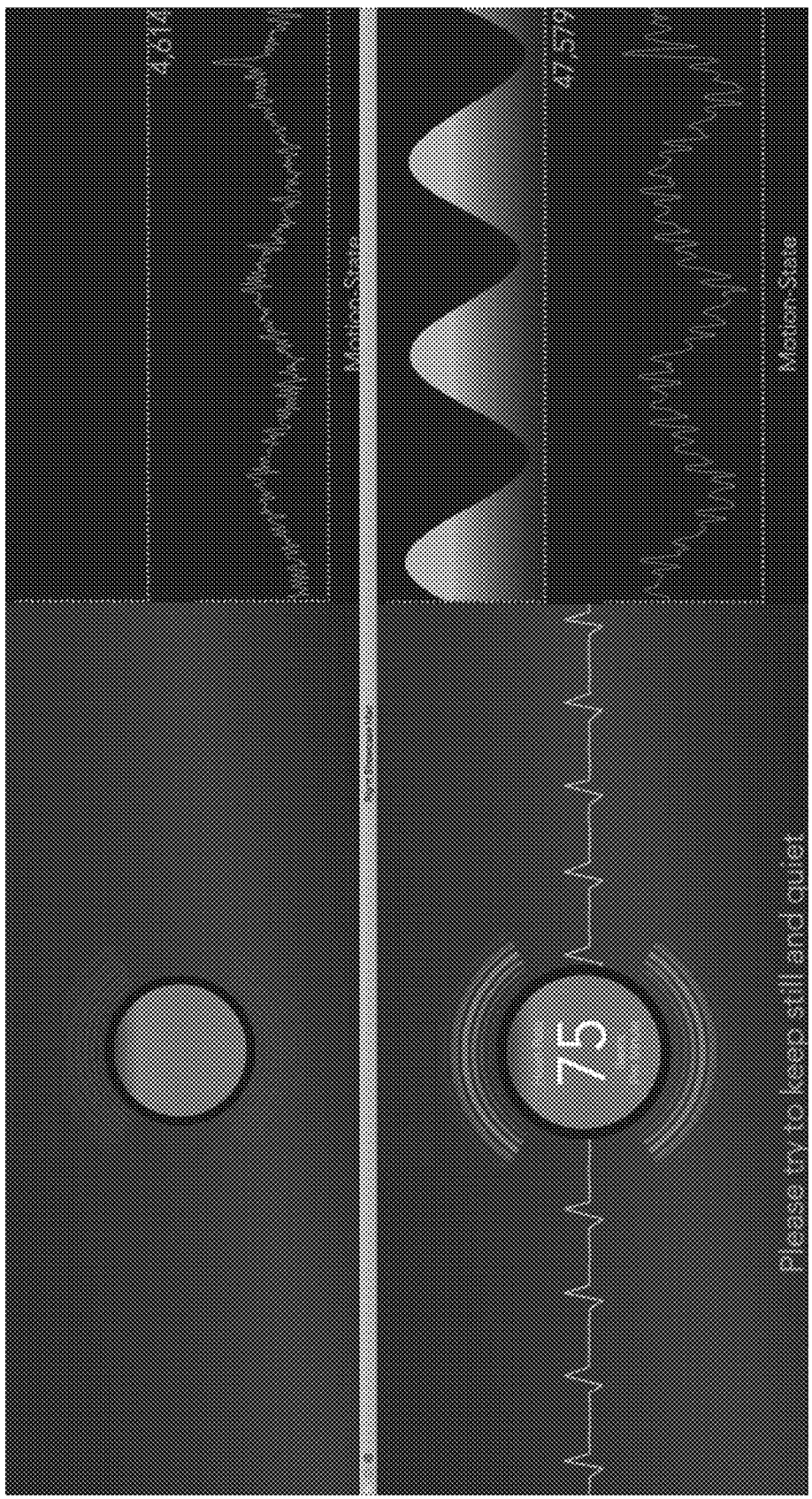
FIGS. 7B-7E show exemplary data sets from the system.
Figure 7C:
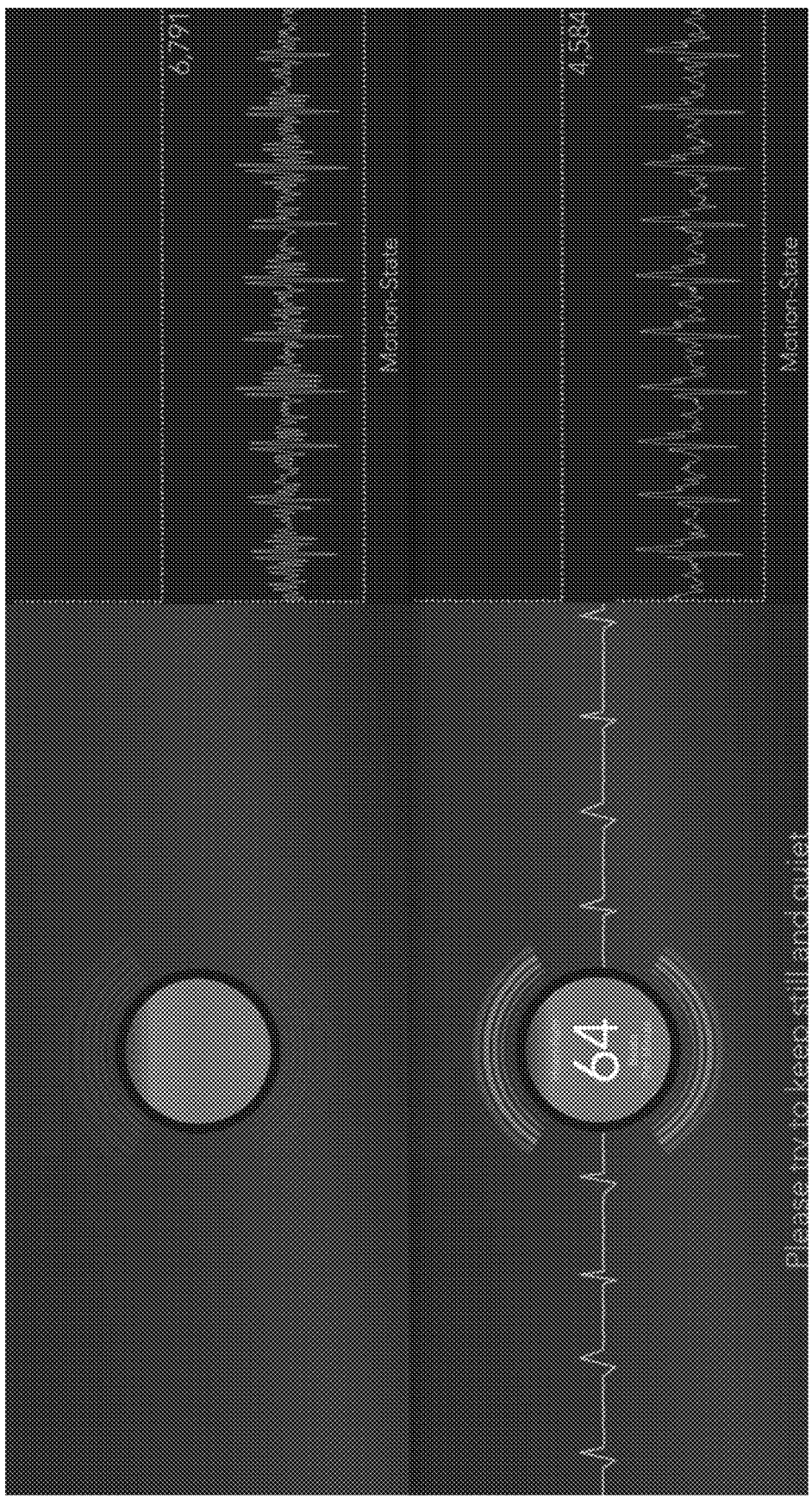

FIGS. 7B-7E show exemplary data which may be obtained from the system. FIG. 7B shows a single sleeper. As can be seen, the motion data is detected by both sensors. However, the system is able to use the correlation of the signals to extract heart rate and respiration data, as well as motion data for the single user. Because the data sets are perfectly correlated, the system is able to determine that there is a single sleeper. FIG. 7C shows the single sleeper holding his or her breath. The respiration data is no longer present. Because of this, the heart rate data is much more visible in the motion state, as can be seen.

Figure 7D:
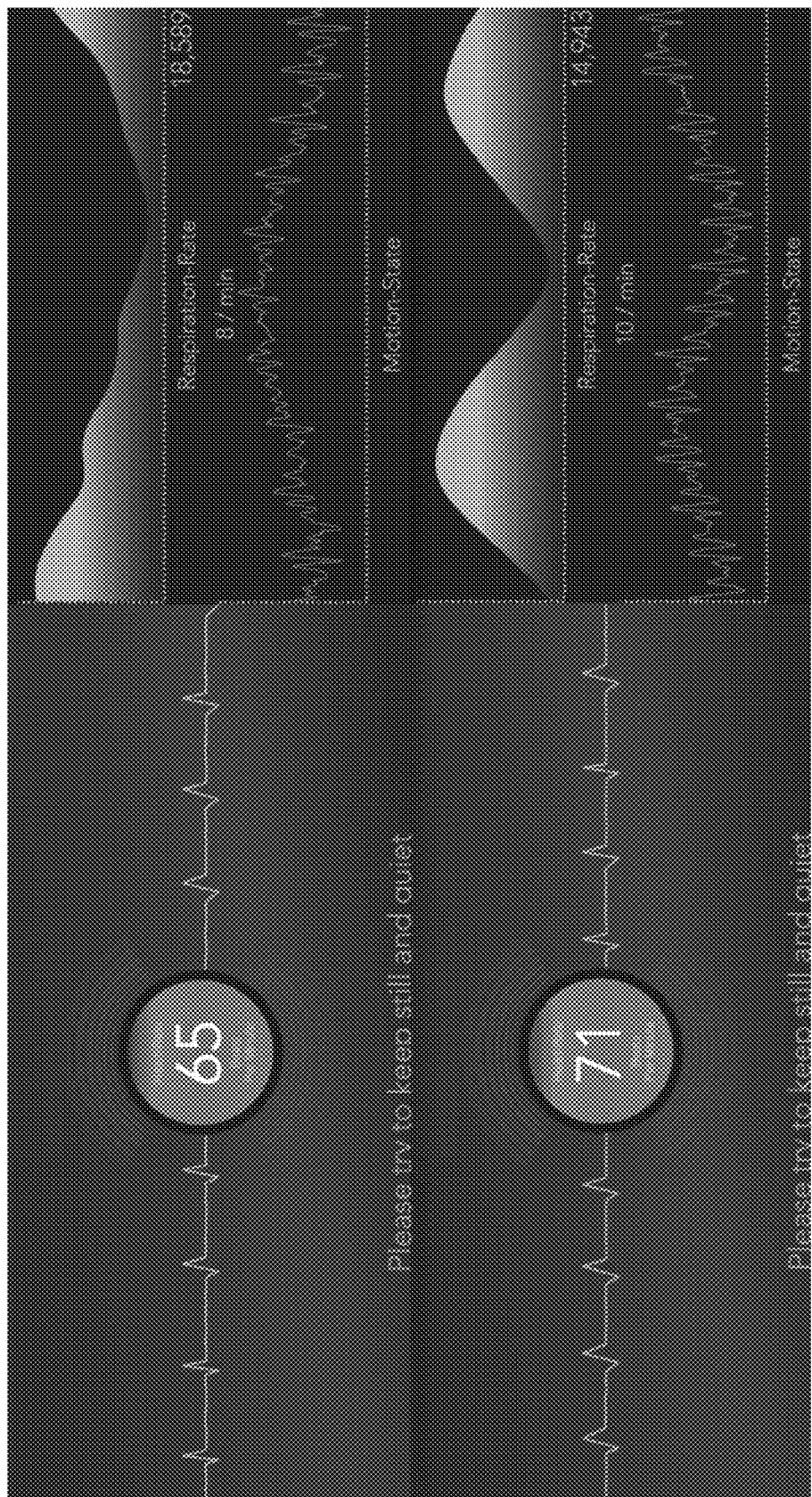
Figure 7E:
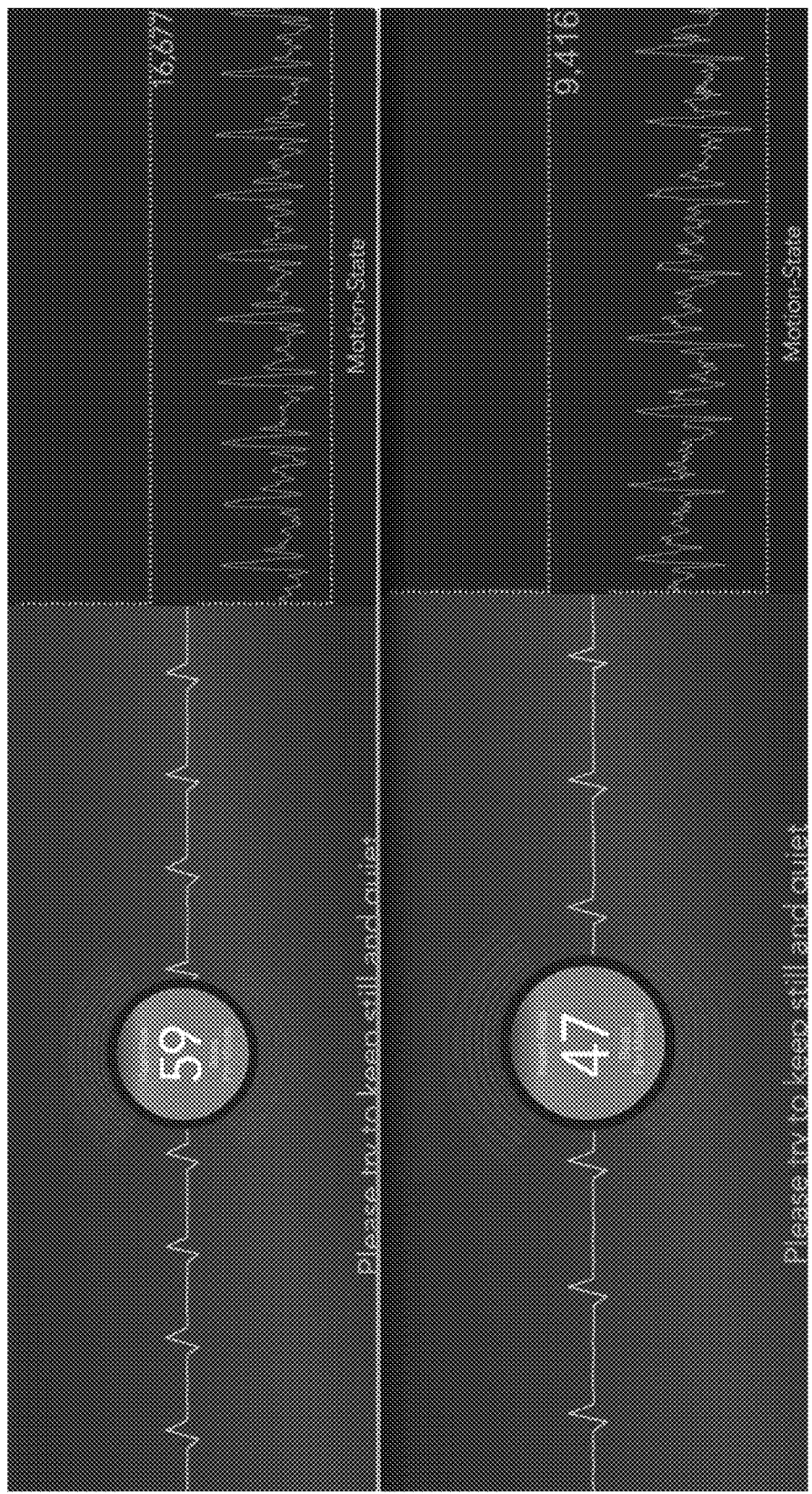

FIG. 7D shows two sleepers. As can be seen, while the motion state data provides information that includes overlap (e.g. both sensors still sense motion from both sleepers) by separating the data sets, the heart rates and respiration rates of each of the users can be successfully identified. This enables the system to track data for each individual user. FIG. 7E illustrates the two sleepers holding their breath. As can be seen, the system detects the lack of respiration. The motion state data more clearly corresponds to the heart rate of the users. Though when examined carefully, the motion-state data for each sensor reflects the heart rate data. Of course in these examples, the users were keeping motionless. When users move, their motions are also reflected in the motion-state data.

In one embodiment, all of these data elements are stored, and may be used in later analysis to identify health conditions, sleep patterns, and potentially other facts that may impact the user's life or health. In one embodiment, because the sensors are very sensitive, even various issues such as hiccups or restless leg syndrome or sleep paralysis. In one embodiment, in addition to making this information available to the user, the system may also utilize this information to optimize the user's sleep quality.

Figure 8:
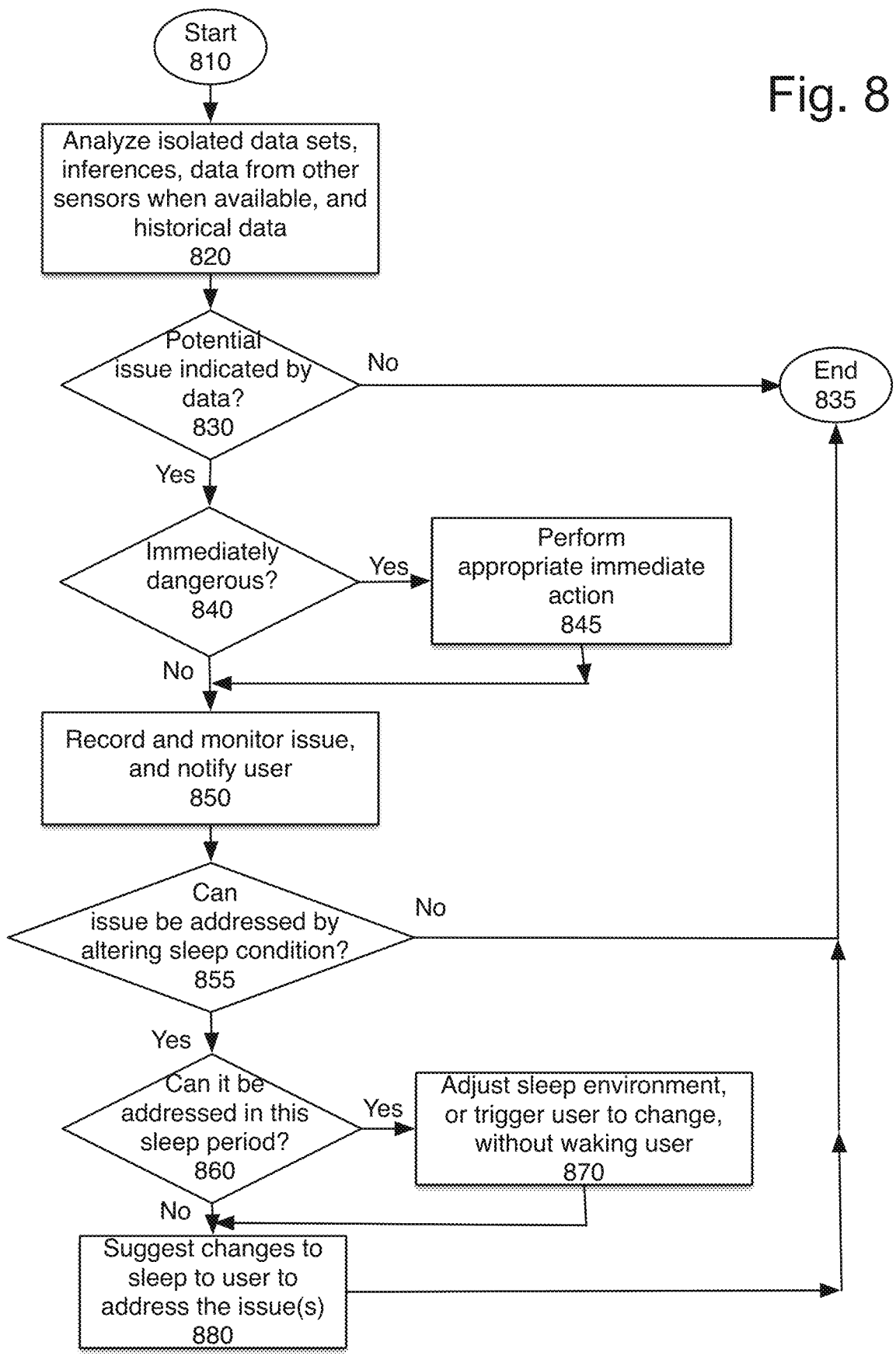
FIG. 8 is a flowchart of one embodiment of identifying potential health issues based on data from the sensor system.

FIG. 8 is a flowchart of one embodiment of identifying potential health issues based on data from the sensor system. The process starts at block 810. In one embodiment, the data obtained from the monitoring system provides information including movements, heart rates, breathing, apnea, snoring, twitching, asymmetry, and other data that may be used to identify health issues.

In one embodiment, the system monitors the user continuously, for sleep phase, and also monitors for any health issues. In one embodiment, the system utilizes a combination of the sleep sensors, base station, sleep analysis system, and/or mobile device to obtain data. For example, in one embodiment, the base station and/or mobile device is used for recording sounds, which may be useful for identifying and/or analyzing snoring, coughing, scratching, apnea, or other conditions. In one embodiment, the sensor data from various sources is integrated to form a complete picture. In one embodiment, the analytics system may turn on the various supporting sensors, as needed. For example, the sleep sensor system may be on, and when the detected movement of the breath indicates that the user may be snoring, the system turns on the recording, within the base station or in an associated mobile device, to record audio data. Similarly, other sensors may be switched into the loop.

At block 820, the isolated data sets, inferences, data from other sensors is analyzed, when available. The data sets, in one embodiment, include the heart beat data (which includes heart rate, and any arrhythmia or other deviations from the standard cardiac cycle), breathing data (which includes snoring, apnea, and other information derived from the movement data), motion data, and micro-movement data. The derived data includes sleep phase data, symmetry data which indicates the symmetry of movements, sleep cycle patterns, the time the user and other data derived from the above data sets. Additionally, the system may utilize environmental data in its analysis. This may include local data such as the angle of the bed, the light level, temperature, humidity, etc. The system further uses data over time, to analyze for changes in the user's sleeping patterns, and changes in breathing or heart measurements that may indicate a potential health condition. For example, if a user over time starts to develop a tremor, starts to have intermittent apnea, starts to sleep badly, this may be detected by the system.

In one embodiment, at block 830 the process determines whether there is any potential issue indicated by the data. If no potential issue is indicated, the process ends at block 835. This process continuously analyzes the data sets available, to identify actual and potential problems. In one embodiment, anonymized data is shared with the system. This may be used to identify precursor data which precedes, and indicates a later developing problem. For example, the system may determine based on a large sample set that people who stop being able to sleep horizontally tend to develop detectable apnea after some time. Because the system learns from the patterns observed, and correlates them over many users and many sleep sessions, such data can be identified.

If there is a potential issue, at block 840 the process determines whether the issue is immediately dangerous. For example, if the user is choking, or has severe enough apnea, or there is a heart arrhythmia that may indicate a heart attack, the system identifies the issue as immediately dangerous, in one embodiment. If so, at block 845, and immediate action is taken. In one embodiment, an immediate action may be an attempt to rouse the user. In one embodiment, an immediate action may be to alert a third party, such as another sleeper or 911. In one embodiment, the immediate action may be to wake another person in the house who could check on the user. The process then continues to block 850. If the identified issue is not immediately dangerous, the process continues directly to block 850.

At block 850, the data for the issue is recorded, and monitored. The user is informed, in one embodiment upon waking. In one embodiment, the data is made available to the user so that the user can forward the information to his or her doctor.

At block 855, the process determines whether the issue can be addressed—cured or improved—by altering a sleep condition. For example, certain congestion issues can be fixed by using a thicker pillow or adjusting the adjustable bed to elevate the user's head. Similarly, some early apnea issues can be avoided if the sleeper does not sleep on his or her back. If the issue can't be addressed, the process ends at block 835. In one embodiment, the user may be alerted to find another method of addressing the detected problem.

If the process could be addressed, at block 860, the process determines whether the issue can be addressed in this sleep period. In one embodiment, using the smart phone Internet of Things system, the system is capable of adjusting certain sleep conditions. Thus, in one embodiment, the system may be able to alleviate the user's issues by adjusting one or more aspects of the sleep environment. For example, the system may turn on an air filter, adjust the inline of the bed, turn on or off lights or sounds, open or close blinds or even windows or doors, etc. In one embodiment, the system may be able to use light, motion, and/or sound guide the user to a different sleep state, which may address a condition as well.

If the condition can be addressed, the sleep environment may be adjusted, or the user may be triggered to change, without waking the user, at block 870. In one embodiment, the process then continues to block 880. At block 880, changes are suggested to the user to address the identified issue(s). These suggestions may include changing the sleep environment, visiting a doctor, altering behaviors, such as increasing exercise or changing eating habits, etc. The process then ends, at block 835.

One of ordinary skill in the art will recognize that the processes described in the above flowcharts are conceptual representations of the operations used. The specific operations of the processes may not be performed in the order shown and described. For example and in one embodiment, the process is interrupt driven, rather than sequentially testing for various occurrences. In one embodiment, data is received or processed in a different order. The specific operations may not be performed in one continuous series of operations, and different specific operations may be performed in different embodiments. Additional operations may be performed, or some operations may be skipped. Furthermore, the processes could be implemented using several sub-processes, or as part of a larger macro process. For instance, in some embodiments, the processes shown in these flowcharts are performed by one or more software applications that execute on one or more computing devices.

Figure 9:
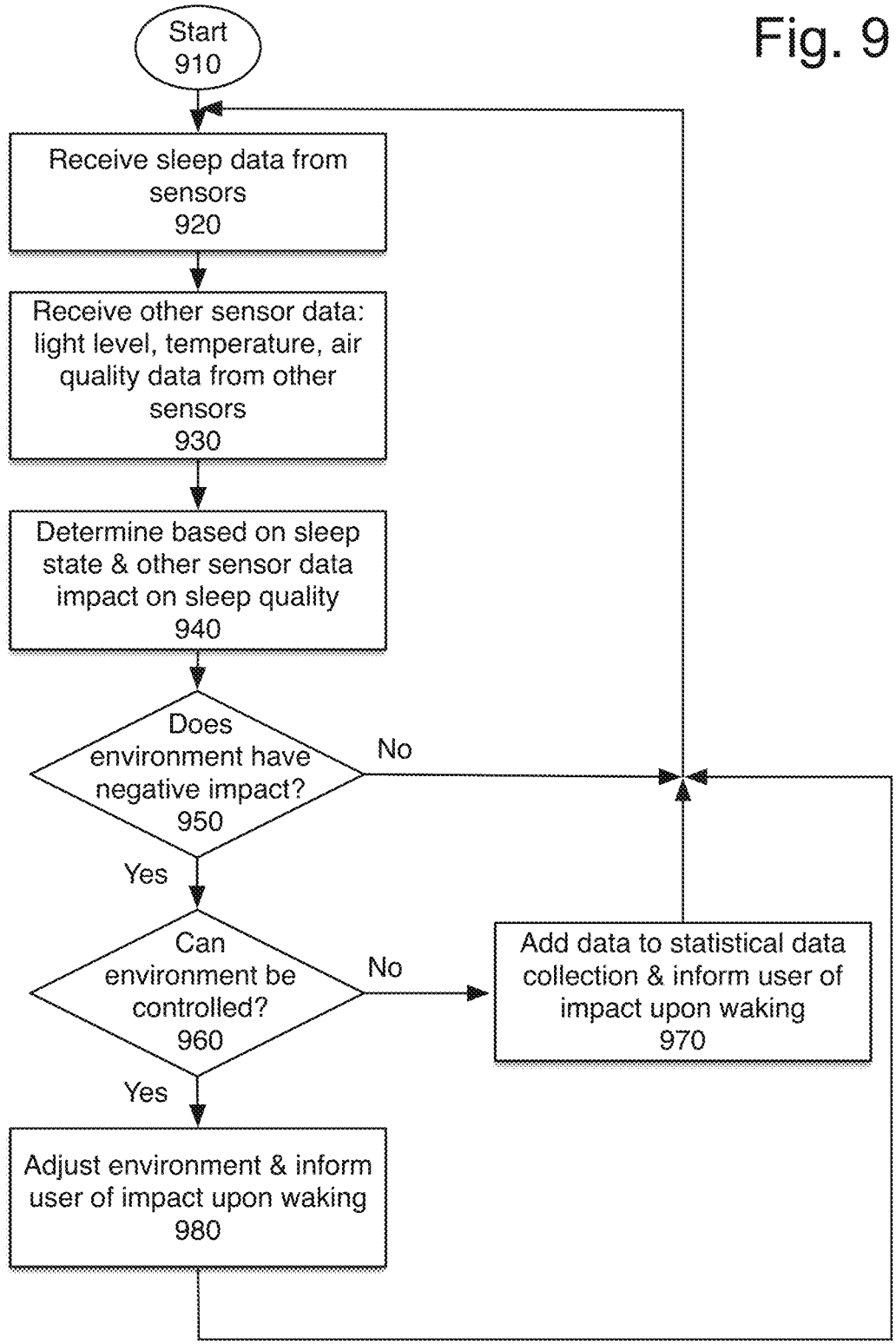
FIG. 9 is a flowchart of one embodiment of data integration, for an Internet of Things (IoT) system.

FIG. 9 is a flowchart of one embodiment of data integration, for an Internet of Things (IoT) system. The process starts at block 910. At block 910, sleep data is received from the sensors. As noted above, the sleep data from two sensors is integrated to separate heart rate, breathing, micro-motion data. As noted above, isolating the data sets leaves data from any medical conditions, such as heart arrhythmia, sleep apnea, restless leg, and other syndromes that can be identified.

At block 930, other sensor is received. In one embodiment, this other data set is received from the base station. The other sensor data includes one or more of light level, temperature, air quality data.

At block 940, the system determines, based on the sleep state and other sensor data, the impact of the environment on the sleep quality. In one embodiment, this is done by evaluation of the actual sleep quality (e.g. depth of sleep, length of each sleep state, restlessness) and a comparison of the sleep states compared to the predicted sleep states.

At block 950, the system determines whether the environment has a negative impact on the sleep quality, sleep state, or sleep quantity. If it does not have a negative impact, the process continues to monitor at block 920.

If there is a negative impact (e.g. the sleep state is not the expected sleep state, and the quality of the sleep is worse than is expected), the process at block 960 determines whether the environment can be controlled. The environment can be controlled if one or more devices in the user's home are controlled via the Internet of Things. If the environment cannot be controlled, or at least the aspect having a negative impact cannot be controlled, at block 970 the data is added to the statistical data collection. The user may be informed of the impact, and remediation may be suggested when the user is awake. For example, if the issue is that the user left the window closed, and the air quality is poor and causing the user to sleep badly, the user may be informed to either turn on an air filter, or open a window. In one embodiment, the system may suggest the addition of devices. In one embodiment, the system may suggest connection of devices to the Internet of Things (e.g. providing control of the device to the system.) The process then continues monitoring, at block 920.

If the environment can be controlled, at block 980 the environment is adjusted. The adjustment may include one or more of: changing the temperature, changing the humidity, turning on or of an air filter, turning on or off white noise, turning on or off lights, changing light temperature, turning on or off music. In one embodiment, one or more of these elements may be provided by the base station. In one embodiment, one or more of these elements may be provided by IoT controllers. The process continues to monitor the user, at block 920.

Figure 10:
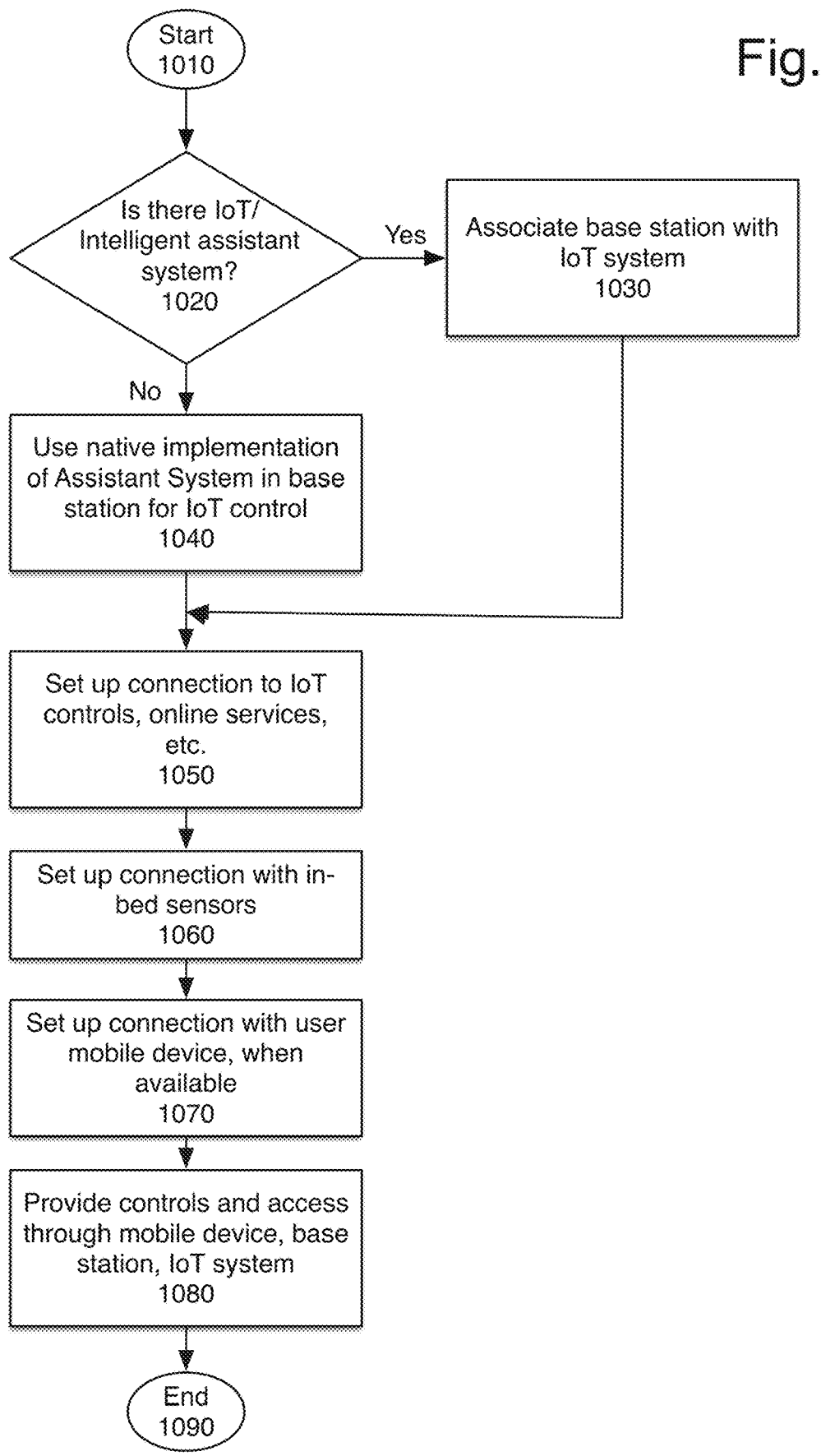
FIG. 10 is a flowchart of one embodiment of setting up the base station.

FIG. 10 is a flowchart of one embodiment of setting up the base station. In one embodiment, the base station is an add-on element, which provides additional sensors and controls to the system. The process starts at block 1010.

At block 1020, the process determines whether there is an existing intelligent assistant system available in the environment. The intelligent assistant system includes, for example AMAZON ALEXA™.

If there is an existing IoT/intelligent assistant system, the process at block 1030 associates the base station with the IoT system. This enables the base station to control the IoT elements. In one embodiment, this also enables the user to utilize base station to control the intelligent assistant, and the IoT devices. In one embodiment, the base station may provide an additional point of control, in addition to a mobile device, and the station of the intelligent assistant system. If the process then continues to block 1050.

If there is no intelligent assistant system, at block 1040, a native implementation of the Assistant system may be invoked in the base station. This enables the base station to act as a virtual Assistant System.

At block 1050, connections to the IoT controls within the home are established. In one embodiment, for security, IoT systems must be paired with the controllers. This reduces the risk of external take-over of the IoT systems (making it less likely that a hacker can control a home). In one embodiment, a secure pairing set-up is used.

At block 1060, the base station is connected to the in-bed sensors. In one embodiment, this is done by plugging the base device into the sleep tracker processor. In one embodiment, the plug-in may be a physical connection, and the base station may be powered through the sleep tracker processor. Alternatively a wireless pairing may be used, and the base station may be separately powered.

At block 1070, the system is connected to a mobile device, when available. In one embodiment, an application is downloaded to the mobile device, and the application is paired with the base station.

At block 1080, the systems are interconnected. In one embodiment, the IoT system, mobile device, and base station are interconnected. In one embodiment, this enables the control of the IoT system and the sleep system through all three pathways (sleep tracker processor, base station/virtual assistant system, and mobile device). The process then ends at block 1090.

Figure 11:
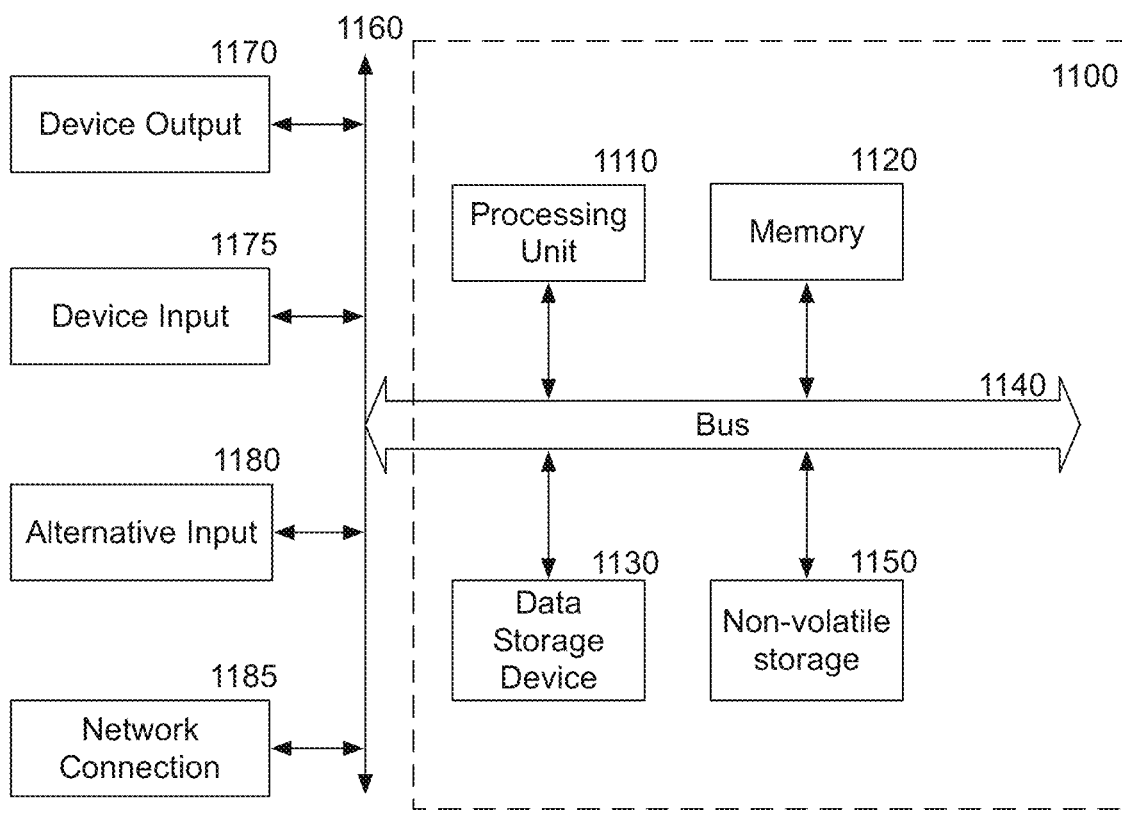
FIG. 11 is a block diagram of a computer system that may be used with the present invention.

FIG. 11 is a block diagram of one embodiment of a computer system that may be used with the present invention. It will be apparent to those of ordinary skill in the art, however that other alternative systems of various system architectures may also be used.

The data processing system illustrated in FIG. 11 includes a bus or other internal communication means 1140 for communicating information, and a processing unit 1110 coupled to the bus 1140 for processing information. The processing unit 1110 may be a central processing unit (CPU), a digital signal processor (DSP), or another type of processing unit 1110.

The system further includes, in one embodiment, a random access memory (RAM) or other volatile storage device 1120 (referred to as memory), coupled to bus 1140 for storing information and instructions to be executed by processor 1110. Main memory 1120 may also be used for storing temporary variables or other intermediate information during execution of instructions by processing unit 1110.

The system also comprises in one embodiment a read only memory (ROM) 1150 and/or static storage device 1150 coupled to bus 1140 for storing static information and instructions for processor 1110. In one embodiment, the system also includes a data storage device 1130 such as a magnetic disk or optical disk and its corresponding disk drive, or Flash memory or other storage which is capable of storing data when no power is supplied to the system. Data storage device 1130 in one embodiment is coupled to bus 1140 for storing information and instructions.

The system may further be coupled to an output device 1170, such as a cathode ray tube (CRT) or a liquid crystal display (LCD) coupled to bus 1140 through bus 1160 for outputting information. The output device 1170 may be a visual output device, an audio output device, and/or tactile output device (e.g. vibrations, etc.)

An input device 1175 may be coupled to the bus 1160. The input device 1175 may be an alphanumeric input device, such as a keyboard including alphanumeric and other keys, for enabling a user to communicate information and command selections to processing unit 1110. An additional user input device 1180 may further be included. One such user input device 1180 is cursor control device 1180, such as a mouse, a trackball, stylus, cursor direction keys, or touch screen, may be coupled to bus 1140 through bus 1160 for communicating direction information and command selections to processing unit 1110, and for controlling movement on display device 1170.

Another device, which may optionally be coupled to computer system 1100, is a network device 1185 for accessing other nodes of a distributed system via a network. The communication device 1185 may include any of a number of commercially available networking peripheral devices such as those used for coupling to an Ethernet, token ring, Internet, or wide area network, personal area network, wireless network or other method of accessing other devices. The communication device 1185 may further be a null-modem connection, or any other mechanism that provides connectivity between the computer system 1100 and the outside world.

Note that any or all of the components of this system illustrated in FIG. 11 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 1120, mass storage device 1130, or other storage medium locally or remotely accessible to processor 1110.

It will be apparent to those of ordinary skill in the art that the system, method, and process described herein can be implemented as software stored in main memory 1120 or read only memory 1150 and executed by processor 1110. This control logic or software may also be resident on an article of manufacture comprising a computer readable medium having computer readable program code embodied therein and being readable by the mass storage device 1130 and for causing the processor 1110 to operate in accordance with the methods and teachings herein.

The present invention may also be embodied in a handheld or portable device containing a subset of the computer hardware components described above. For example, the handheld device may be configured to contain only the bus 1140, the processor 1110, and memory 1150 and/or 1120.

The handheld device may be configured to include a set of buttons or input signaling components with which a user may select from a set of available options. These could be considered input device #1 1175 or input device #2 1180. The handheld device may also be configured to include an output device 1170 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a kiosk or a vehicle. For example, the appliance may include a processing unit 1110, a data storage device 1130, a bus 1140, and memory 1120, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 1185.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1110. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

FIG. 10 is one embodiment of a circuit diagram of an inductive sensor system that may be used with the present invention. The sensor, in one embodiment, receives power from circuit LDC1000, and sends signal data back to LDC1000. The LDC1000 is coupled to a microprocessor, which includes either on-board or coupled memory to store data. Power converter provides power to LDC1000. In one embodiment, the power converter provides low power AC to the sensor as well as DC power to the microprocessor and circuit LDC1000. In one embodiment, the sensor and LDC1000 are placed into the box spring or mattress, while the microprocessor and power converter are coupled via a cable such as a CAT5 cable. In one embodiment, microprocessor, memory, and power converter are plugged into the wall, and provide processing of the data. In one embodiment, microprocessor may include a network connectivity capability. Alternatively, the network connection may be external to the microprocessor, but part of the sensor system.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A method comprising:
   collecting data by a first sleep sensor and a second sleep sensor placed on either side of a sleep surface;
   comparing by a sleep tracker processor the data from the first sleep sensor and the data from the second sleep sensor, to determine whether there is one sleeper or two sleepers on the sleep surface;
   when the sleep tracker processor determines that there is the one sleeper on the sleep surface:
      identifying the data collected by the first sleep sensor as associated with the one sleeper;
      adding the data collected by the second sleep sensor to the data from the first sleep sensor, to produce enhanced data for the one sleeper;
      analyzing the enhanced data to identify the one sleeper's sleep phase;
   when the sleep tracker processor determines that there is a first sleeper and a second sleeper on the sleep surface:
      identifying a first portion of the data collected by the first sleep sensor as data associated with the first sleeper; and
      removing the data associated with the first sleeper from the data collected by the second sleep sensor, to identify a second portion of the data, the second portion of the data associated with the second sleeper; and
      using the first portion of the data to identify the sleep phase of the first sleeper; and
      using a second portion of the data to identify the sleep phase of the second sleeper.

2. The method of claim 1, where the first sleep sensor comprises a piezoelectric sensor in a sensor case.

3. The method of claim 1, further comprising:
   separating out a first sub-portion of the data associated with a heart beat of the first sleeper,
   separating out a second sub-portion of the data associated with a breathing of the first sleeper, and
   utilizing the first sub-portion, the second sub-portion, and a third sub-portion of the data associated with the movement of the sleeper, to identify the sleep phase of the first sleeper.

4. The method of claim 1, further comprising:
   providing sleep data to the first sleeper on a user mobile device.

5. The method of claim 1, further comprising:
   enabling control of Internet of Things (IoT) elements in an environment of the sleep surface, to optimize sleep quality of the first sleeper.

6. The method of claim 5, wherein the IoT elements are controlled based on a combination of the sleep phase of the first sleeper and a second sleeper.

7. The method of claim 1, further comprising:
   receiving environmental data from a base station; and
   utilizing the environmental data in conjunction with the first portion of the data to determine the first sleeper's sleep phase.

8. The method of claim 7, wherein the base station is used to adjust an environment to improve sleep quality of the first sleeper.

9. A sleep tracking system comprising:
   a first in-bed sensor for positioning on a first side of a sleep surface;
   a second in-bed sensor for positioning on a second side of the sleep surface; and
   a sleep tracker processor comprising software to:
      determine a number of sleepers on the sleep surface, wherein the number of sleepers is one or more, based on data from the first in-bed sensor and the second in-bed sensor;
      when the sleep tracker processor identifies a first sleeper and a second sleeper on the sleep surface:
         identify a first portion of the data collected by the first in-bed sensor associated with a first sleeper;
         identify a second portion of the data collected by the second in-bed sensor associated with the second sleeper, and
         remove the data associated with the first sleeper from the data collected by the second in-bed sensor, to identify a sub-portion of the second portion of the data associated with the second sleeper; and
      when the sleep tracker processor determines that the second sleeper is not on the sleep surface, adding the data from the second in-bed sensor to the data from the first in-bed sensor, to create an enhanced data set for the first sleeper.

10. The sleep tracking system of claim 9, further comprising:
    the sleep tracker processor further comprising software to identify a third portion of the data collected by a second in-bed sensor associated with a first sleeper, and removing data associated with the second sleeper from the data collected by the second in-bed sensor, adding the third portion of the data from the second in-bed sensor to the data from the first in-bed sensor, to create an enhanced data set for the first sleeper.

11. The sleep tracking system of claim 9, where the first in-bed sensor comprises a piezoelectric sensor in a sensor case.

12. The sleep tracking system of claim 9, wherein the sleep tracker processor further comprises software to:
    perform a ballistocardiograph analysis to separate out a first sub-portion of the data from the first in-bed sensor and the second in-bed sensor associated with a heart beat of the first sleeper, and separate out a second sub-portion of the data from the first in-bed sensor and the second in-bed sensor associated with a breathing of the first sleeper.

13. The sleep tracking system of claim 9, further comprising:
a server system to provide sleep data to the first sleeper on a user mobile device.

14. The sleep tracking system of claim 9, further comprising:
an IoT controller to enable control of Internet of Things (IoT) elements in an environment of the sleep surface, to optimize sleep quality.

15. The sleep tracking system of claim 9, further comprising:
a base station including one or more sensors to collect environmental data; and
the sleep tracker processor utilizing the environmental data in conjunction with the first portion of the data to determine the first sleeper's sleep phase.

16. The sleep tracking system of claim 15, wherein the base station is used to adjust an environment to improve sleep quality of the first sleeper.

17. A sleep tracking system comprising:
a first in-bed sensor for positioning at head height for a first sleeper on a first side of a sleep surface;
a second in-bed sensor for positioning at head height for a second sleeper on a second side of the sleep surface; and
a sleep tracker comprising software:
to determine whether there is a second sleeper on the sleep surface; and
when it is determined that there is a second sleeper on the sleep surface:
identifying a first portion of the data associated with the first sleeper and a second portion of the data associated with the second sleeper, based on data from the first in-bed sensor and the second in-bed sensor, and
analyzing the first portion and the second portion of the data to identify a sleep phase for the first sleeper and the second sleeper;
when the sleep tracker determines that the second sleeper is not on the sleep surface, adding data from the second in-bed sensor to the data from the first in-bed sensor, thereby enhancing the data for the first sleeper from the first sensor with the data collected by the second sensor.

18. The method of claim 1, further comprising:
identifying when a second sleeper gets on the bed, while the system is monitoring the first sleeper, and switching the sleep tracker processor to utilize multi-user adjustment.

19. The method of claim 1, further comprising:
receiving predicted sleep phase data from a server;
verifying the predicted sleep phase data with the identified sleep phase of the sleepers on the sleep surface.

* * * * *